US007655465B2

(12) United States Patent
Sherley et al.

(10) Patent No.: US 7,655,465 B2
(45) Date of Patent: Feb. 2, 2010

(54) METHODS FOR EX VIVO PROPAGATION OF SOMATIC HAIR FOLLICLE STEM CELLS

(75) Inventors: James L. Sherley, Boston, MA (US); Johnathan King, Plano, TX (US)

(73) Assignee: Massachusetts Institute of Technology, Cambridge, MA (US)

( * ) Notice: Subject to any disclaimer, the term of this patent is extended or adjusted under 35 U.S.C. 154(b) by 348 days.

(21) Appl. No.: 11/147,013

(22) Filed: Jun. 7, 2005

(65) Prior Publication Data

US 2005/0272147 A1 Dec. 8, 2005

Related U.S. Application Data

(60) Provisional application No. 60/577,532, filed on Jun. 7, 2004.

(51) Int. Cl.
*C12N 5/06* (2006.01)

(52) U.S. Cl. .................... 435/377; 435/325; 435/375; 435/378; 514/263.34

(58) Field of Classification Search .................. None
See application file for complete search history.

(56) References Cited

U.S. PATENT DOCUMENTS

| 5,474,931 | A | 12/1995 | DiSorbo et al. |
|---|---|---|---|
| 5,741,646 | A | 4/1998 | Sherley et al. |
| 5,801,159 | A | 9/1998 | Miller et al. |
| 6,146,889 | A | 11/2000 | Reid et al. |
| 6,242,252 | B1 | 6/2001 | Reid et al. |
| 2003/0133918 | A1 | 7/2003 | Sherley |
| 2004/0018620 | A1 | 1/2004 | Sherley |
| 2005/0074874 | A1 | 4/2005 | Sherley |

FOREIGN PATENT DOCUMENTS

| WO | WO 97/24458 A1 | 7/1997 |
|---|---|---|
| WO | WO 02/062969 A2 | 8/2002 |
| WO | WO 02/090992 A2 | 11/2002 |
| WO | WO 03/069972 A2 | 8/2003 |

OTHER PUBLICATIONS

Sherley, J.L. "Adult Stem Cell Differentiation: What Does It Mean?" Proceedings of the Second Joint EMBS/BMES Conference; Houston, TX, USA, Oct. 23-26, 2002, pp. 741-742.*

ATCC; Cell Lines and Hybridomas; $8^{th}$ ed.; p. 518 (1994).
Bartel, T. et al.; Biochimica et Biophysica Acta.; 1035:331-339 (1990).
Brenner, M. K.; Gene Transfer to Hematopoietic Cells; New Engl. J. Med.; 335(5):337-339 (1996).
Cairns, J.; Mutation Selection and the Natural History of Cancer; Nature; 255:197-200 (May 15, 1975).
Fuchs, E. and Segre, J. A.; Stem Cells: A New Lease on Life; Cell; 100:143-155 (Jan. 7, 2000).
Ganassin, R.C. et al.; Journal of Cellular Physiology; 160:409-416 (1994).
Gridelli, B. and Remuzzi, G.; Strategies for Making More Organs Available for Transplantation; New Engl. J. Med.; 343(6):404-410 (Aug. 10, 2000).
Hayashi, Y. et al.; Experimental Cell Research; 185:217-228 (1989).
Hirai, S. et al., Biochemical Pharmacology; 45(8):1695-1701 (1993).
Lee, Hsuan-Shu et al.; Clonal Expansion of Adult Rat Hepatic Stem Cell Lines by Suppression of Asymmetric Cell Kinetics (SACK); Biotechnology and Bioengineering; 83(7):760-771 (Sep. 30, 2003).
Liu, Y., Bohn, S.A., and Sherley, J.L.; Inosine-5'-Monophosphate Dehydrogenase is a Rate-Determining Factor for p53-Dependent Growth Regulation; Molecular Biology of the Cell; 9:15-28 (1998).
Liu, Y., Riley, L.B., Bohn, S.A., Boice, J.A., Stadler, P.B., and Sherley, J.L.; Comparison of Bax, Waf1, and IMP Dehydrogenase Regulation in Response of Wild-Type p53 Expression Under Normal Growth Conditions; Journal of Cellular Physiology; 177:364-376 (1998).
Loeffler, M. and Potten, C.S.; Stem Cells and Cellular Pedigrees—A Conceptual Introduction; Stem Cells; (San Diego, CA: Harcourt Brace & Co.), pp. 1-27 (1997).
Merok, J.R. and Sherley, J.L.; Breaching the Kinetic Barrier to In Vitro Somatic Stem Cell Propagation; Journal of Biomedicine Biotechnology; 1(1):25-27 (2001).

(Continued)

*Primary Examiner*—Allison M Ford
(74) *Attorney, Agent, or Firm*—Nixon Peabody LLP

(57) ABSTRACT

The present invention is directed to methods for readily propagating somatic hair follicle stem cells or melanocyte stem cells. The methods comprise enhancing guanine nucleotide (GNP) biosynthesis, thereby expanding guanine nucleotide pools. This in turn conditionally suppresses asymmetric cell kinetics in the explanted cells. The methods of the invention include pharmacological methods and genetic methods. For example, the resulting cultured somatic hair follicle stem cells can be used for a variety of applications including cell replacement therapies such as hair transplants, gene therapies, and tissue engineering applications, such as the generation of artificial skin and skin regeneration strategies including skin grafts.

6 Claims, 10 Drawing Sheets

OTHER PUBLICATIONS

Moore, K.A. et al..; In Vitro Maintenance of Highly Purified, Transplantable Hematopoietic Stem Cells; Blood; 89(12):4337-4347 (Jun. 15, 1997).

Phillips, R.L., Ernst, R.E., Brunk, B., Ivanova, N., Mahan, M.A., Deanehan, J.K., Moore, K.A., Overton, G.C., and Lemischka, I.R.; The Genetic Program of Hematopoietic Stem Cells; Science; 288:1635-1640 (Jun. 2, 2000).

Podolsky, D.K.; Regulation of Intestinal Epithelial Proliferation: a Few Answers, Many Questions; American Journal of Physiology; 264:G179-G186 (1993).

Potten, C.S. and Grant, H.K.; The Relationship Between Ionizing Radiation-Induced Apoptosis and Stem Cells in the Small and Large Intestine; British Journal of Cancer; 78(8):993-1003 (1998).

Potten, C.S. and Morris, R.J.; Epithelial Stem Cells In Vivo; J. Cell Sci. Suppl.; 10:45-62 (1988).

Rambhatla, L., Bohn, S.A., Stadler, P.B., Boyd, J.T., Coss, R.A., and Sherley, J.L.; Cellular Senescene: ex vivo p53-Dependent Asymmetric Cell Kinetics; Journal of Biomedicine Biotechnology; 1(1):28-37 (2001).

Reisner, Y., Itzicovitch, L., Meshorere, A., and Sharon, N.; Hemopoietic Stem Cell Transplantation Using Mouse Bone Marrow and Spleen Cells Fractionated by Lectins; Proc. Natl. Acad. Sci. USA; 75(6):2933-2936 (Jun. 1978).

Sherley, J.L.; Guanine Nucleotide Biosynthesis is Regulated by the Cellular p53 Concentration; Journal of Biological Chemistry; 266(36):24815-24828 (1991).

Sherley, J.L., Stadler, P.B. and Stadler, J.S.; A Quantitative Method for the Analysis of Mammalian Cell Proliferation in Culture in Terms of Dividing and Non-dividing cells; Cell Proliferation; 28:137-144 (1995).

Sherley, J.L., Stadler, P.B. and Johnson, D.R.; Expression of the Wildtype p53 Antioncogene Induces Guanine Nucleotide-Dependent Stem Cell Division Kinetics; Proc. Natl. Acad. Sci. USA; 92:136-140 (Jan. 1995).

Sherley, J.L.; IMPDH: A Regulator of Somatic Stem Cell Kinetics; Abstracts of Papers American Chemical Society; 220(1):CARB 10 (2000).

Talbot, N.C. et al.; Cloning and Stem Cells; 6(1):37-47 (Nov. 1, 2004).

Tunstead, J.R. et al.; Molecular Determinants of Asymmetric Stem Cell Kinetics; Developmental Biology; 235(1):227 (Jul. 1, 2001).

Wagers, A.J. et al.; Cell; 116:639-648 (Mar. 5, 2004).

Weissman, I.L.; Stem Cells: Units of Development, Units of Regeneration, and Units in Evolution; Cell; 100(1):157-168 (Jan. 7, 2000).

Wilson, J.M.; Vehicles for Gene Therapy; Nature; 365:691-692 (Oct. 21, 1993).

Zimmermann, S. et al.; Leukemia; 17:1146-1149 (2003).

Morris, R. J. et al.; Nature Biotechnology; 22(4):411-417 (2004.

* cited by examiner

SSC ASYMMETRIC KINETICS IN VIVO

A CELL CULTURE MODEL FOR SSC KINETICS

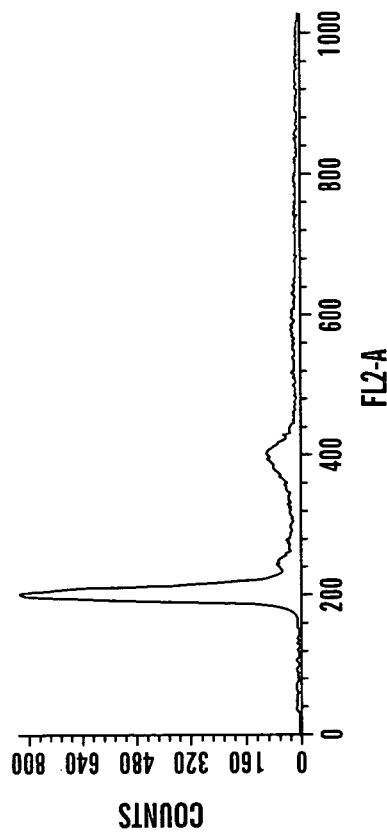
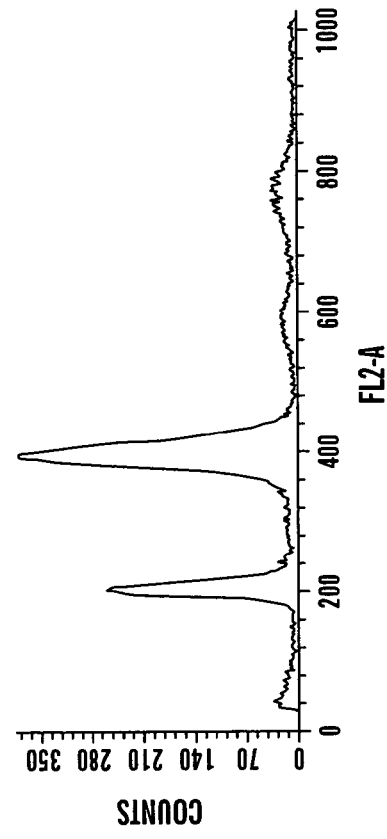
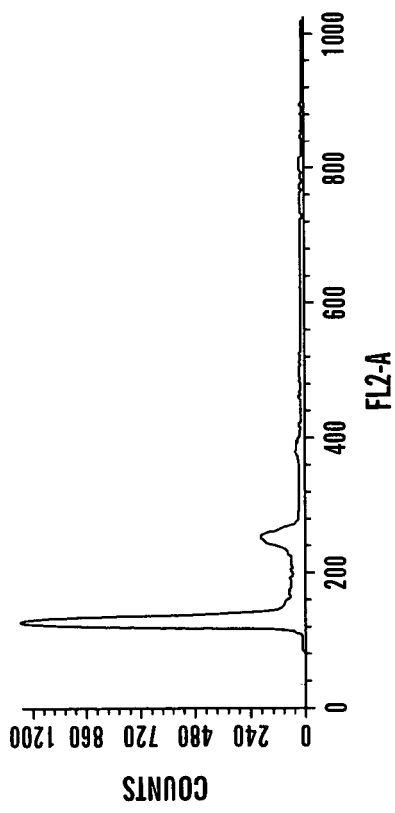
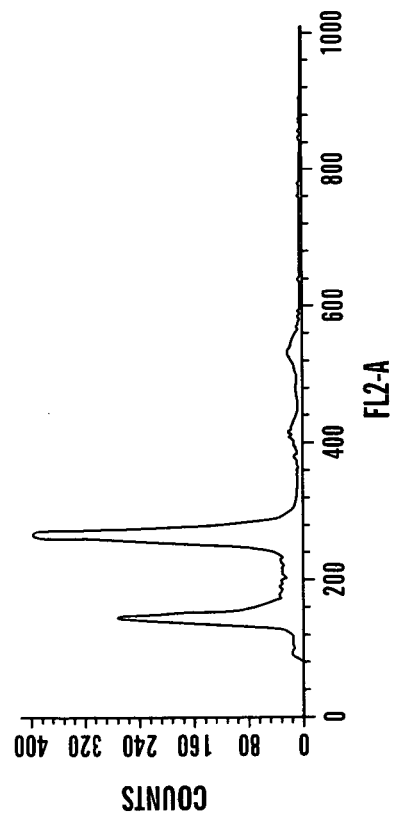
FIG. 10A
FIG. 10B
FIG. 10C
FIG. 10D

METHODS FOR EX VIVO PROPAGATION OF SOMATIC HAIR FOLLICLE STEM CELLS

CROSS-REFERENCE TO RELATED APPLICATIONS

The present application claims the benefit under 35 U.S.C. 119 (e) of the U.S. provisional Patent Application No. 60/577,532, filed Jun. 7, 2004.

GOVERNMENT FUNDING

This invention was supported by National Science Foundation grant 9843342 and the government of the United States has certain rights thereto.

FIELD OF THE INVENTION

The present application is directed to the ex vivo expansion of hair follicle stem cells and melanocyte stem cells and to their use in cell replacement therapies including skin grafts, hair transplantation strategies, and tissue engineering applications. Preferably somatic hair follicle stem cells from human tissue are used.

BACKGROUND OF THE INVENTION

Stem cells have the ability to differentiate into a variety of cells and tissues. Thus, considerable attention has focused on stem cells and their uses in a multitude of applications, including tissue engineering, tissue regeneration, and gene therapy. Stem cells have been isolated from both embryonic and adult tissues. Somatic stem cells that are derived from adult tissue still have the ability to renew adult tissues (Fuchs and Segre, 2000). Thus, in light of the ongoing controversies surrounding the use of embryonic stem cells, the use of somatic stem cells are a particularly attractive alternative.

The presence of stem cells in somatic tissues has been well established using functional tissue cell transplantation assays (Reisner et al., 1978). However, isolation and propagation of somatic stem cells has proven difficult. Methods to isolate and expand stem cells from somatic tissue, particularly without significant differentiation, are highly desirable. There have been some questions raised regarding how multi-potent adult stem cells are related to embryonic stem cells. Thus, it is important to be able to obtain and cultivate many different types of somatic stem cells. In particular, the availability of a method for producing hair follicle stem cells and melanocyte stem cells from adult tissues would greatly contribute to cell replacement therapies and tissue engineering. For example, hair follicle stem cells have the ability to produce hair, sweat glands, sebaceous glands and skin cells (Oshima et al., 2001). One of the problems encountered with artificial skin is that it does not have sweat glands or sebaceous glands, leading to problems with thermo-regulation and dryness, respectively, when large segments are grafted. It would be desirable to have other cells that could be used in tissue engineering applications, such as in the generation of functional skin grafts.

There has been considerable difficulty encountered in obtaining human somatic hair follicle stem cells that can be propagated and cultured ex vivo. One factor is the predominant way somatic stem cells divide is by asymmetric cell kinetics. During asymmetric kinetics, one daughter cell divides with the same kinetics as its stem cell parent, while the second daughter gives rise to a differentiating non-dividing cell lineage. The second daughter may differentiate immediately; or, depending on the tissue, it may undergo a finite number of successive symmetric divisions to give rise to a larger pool of differentiating cells.

Such asymmetric cell kinetics are a major obstacle to somatic cell expansion in vitro (Merok and Sherley, 2001; Rambhatla et al., 2001; Sherley, 2002). In culture, continued asymmetric cell kinetics results in dilution and loss of an initial relatively fixed number of stem cells by the accumulation of much greater numbers of their terminally differentiating progeny. If a sample includes both exponentially growing cells as well as somatic stem cells, the growth of the exponentially growing cells will rapidly overwhelm the somatic stem cells, leading to their dilution. Even in instances where it is possible to select for relatively purer populations, for example by cell sorting, asymmetric cell kinetics prevent expansion.

Another factor is that during the hair growth cycle, the cells are believed to migrate from the bulge region to a place at the base of the hair follicle known as the bulb (Fuchs, 2001). These migratory patterns and the general difficulty of dissecting these regions from hair follicles have foiled attempts to establish hair follicle stem cell lines.

Thus, despite the need for methods to isolate such stem cells from an individual and expand them ex vivo, it has not been possible to do so.

SUMMARY OF THE INVENTION

We have now invented methods for readily propagating somatic hair follicle stem cells and melanocyte stem cells. The methods shift hair follicle stem cells from asymmetric cell kinetics to symmetric cell kinetics, which promote exponential expansion of adult stem cells in culture. Symmetric stem cell kinetics are characterized by divisions that produce two stem cells and no differentiating cells. This shift in kinetics symmetry is referred to as "suppression of asymmetric cell kinetics." The methods comprise enhancing guanine nucleotide (GNP) biosynthesis, thereby expanding guanine nucleotide pools. This in turn conditionally suppresses the asymmetric cell kinetics exhibited by for example somatic hair follicle cells. The methods of the invention include pharmacological methods and genetic methods. One preferred method of enhancing guanine nucleotide biosynthesis is to bypass or override normal inosine-5'-monophosphate dehydrogenase (IMPDH) regulation. IMPDH catalyzes the conversion of inosine-5' monophosphate (IMP) to xanthosine monophosphate (XMP) for guanine nucleotide biosynthesis. This step can be bypassed or overridden by providing a guanine nucleotide precursor (rGNPr) such as xanthosine or hypoxanthine, respectively. The next metabolite in the GNP pathway is guanine monophosphate (GMP), which in turn is metabolized to the cellular guanine nucleotides. The resulting cultured somatic hair follicle stem cells can be used for a variety of applications including cell replacement therapies such as hair transplants, gene therapies, and tissue engineering such as skin grafts.

In one preferred embodiment of the invention, somatic hair follicle stem cells or melanocyte stem cells are removed, preferably hair follicle stem cells, and cultivated in the presence of compounds such as guanine nucleotide precursors (rGNPrs), which lead to increased guanine nucleotide pools. Preferably, the rGNPr is xanthosine or hypoxanthine. Even more preferably, the rGNPr is xanthine.

In another preferred embodiment of the invention, the somatic hair follicle stem cells are propagated in a primitive undifferentiated state but retain the ability to be induced to produce differentiating progeny cells. Differentiation can be induced by the site where the cell is placed in a subject or appropriately engineered material.

Another preferred embodiment provides for deriving clonal lines of somatic hair follicle stem cells by limiting dilution plating or single cell sorting in the presence of compounds which enhance guanine nucleotide biosynthesis, thereby suppressing asymmetric cell kinetics.

In another embodiment of the invention, genes that lead to constitutive upregulation of guanine ribonucleotides (rGNPs) are introduced into the somatic hair follicle stem cells. Preferred genes are those that encode inosine-5'monophosphate dehydrogenase (IMPDH) or xanthine phosphoribosyltransferase (XPRT). More preferably, XPRT.

In yet another embodiment, the guanine nucleotide precursor (rGNPr) such as xanthosine, xanthine and hypoxanthine can be added topically to a subject having hair follicle cells. Preferably one adds a topical substance containing xanthine or hypoxanthine as the active ingredient. One preferred area of topical administration is the scalp.

Another embodiment of the invention provides methods for administering hair follicle stem cells or melanocyte stem cells to a patient in need thereof, comprising the steps of (1) isolating the stem cells from an individual; (2) expanding for example the somatic hair follicle stem cells in culture using pharmacological or genetic methods to enhance guanine nucleotide biosynthesis to expand guanine nucleotide pools and suppress asymmetric cell kinetics; and thereafter, (3) administering the expanded hair follicle stem cells to said individual in need thereof.

Further embodiments of the invention provide for additional manipulations, including genetic manipulation of the somatic hair follicle stem cells or melanocyte stem cells prior to administration to the individual.

Another preferred embodiment provides for the use of expanded somatic hair follicle stem cells or melanocyte stem cells to identify molecular probes specific for such stem cells in tissues or tissue cell preparations.

Another preferred embodiment of the invention provides transgenic non-human animals into whose genome is stably integrated an exogenous DNA sequence comprising a ubiquitously-expressed promoter operably linked to a DNA sequence encoding a protein that leads to constitutive upregulation of guanine nucleotides, including the gene encoding inosine-5'-monophosphate dehydrogenase (IMPDH) or xanthine phophoribosyl transferase (XPRT). Preferably, the transgene is XPRT driven by a ubiquitously expressed promoter. Preferably, the transgenic animal is a mouse.

BRIEF DESCRIPTION OF THE DRAWINGS

FIG. 1A, In vivo, somatic stem cells (SSC, bold-lined circles) can exhibit one of three division programs: 1) Highly restricted symmetric kinetics that produce two similar somatic stem cells (brackets); 2) Dormancy (stippled circle); and 3) Asymmetric kinetics, the most populated somatic stem cell kinetics state in most tissues. Asymmetric somatic stem cells underlie turnover units (TU; Hererro-Jimenez et al., 1998). Turnover units are comprised of three cell types: an asymmetric somatic stem cell, transit cells (thin-lined open circle), and mature, differentiated, non-dividing terminal cells (closed circle). Asymmetric somatic stem cells divide to produce another asymmetric somatic stem cell and a transit cell. Depending on the type of tissue, the transit cell may undergo no further division, or a finite number of successive divisions may occur. However, all transit lineage cells mature into differentiated, non-dividing terminal cells. FIG. 1B, Mde1 cells with conditional asymmetric cell kinetics (due to p53-induced down-regulation of IMPDH) can be induced to switch from symmetric kinetics (left compartment) to two types of asymmetric kinetics programs (right compartment) that have the key features of asymmetric somatic stem cell kinetics in vivo.

FIG. 8A and FIG. 8B show phase micrographs of crystal violet-stained colonies of a Xn-derived clonal hair follicle cell line (40× mag.). FIG. 8A, In the center of colonies, where cells are growth-arrested, a high degree of differentiation is evident by dark purple cells, which contain light-reflective vesicles. FIG. 8B, At the colony edges, where there is active cell growth, few differentiated cells are present.

In FIGS. 9A and 9B, the left major peak corresponds to G1 cells with 2N DNA content. The right major peak corresponds to G2/M cells with 4N DNA content. S phase cells with variable DNA content contribute the fluorescence area between the major two peaks. The G1 peak that remains in FIG. 9D after colcemid arrest reflects the large fraction of arrested cells produced by asymmetric self-renewal in cultures of p53-expressing cells (i.e., IMPDH down-regulated). The colcemid arrest profile of symmetrically cycling p53-null cells (FIG. 9C) is consistent with their known very low fraction of non-cycling cells.

FIGS. 10A-10D shows CAA detection of non-cycling progeny cells in cycling cultures of a mouse hair follicle stem cell line. Lig-8 cells with independently confirmed asymmetric self-renewal (Semino et al., 2003; Lee et al., 2003, 2004) was used as a positive control, FIGS. 10A and 10C. One of three different mouse hair follicle epithelial cell lines (FIGS. 10B and 10D), with independent evidence of sebocyte differentiation, were evaluated. FIGS. 10A and 10B, respective untreated cells under routine growth conditions. FIGS. 10C and 10D, respective colcemid treated cultures. The persistent major left peak at the position of G1 cells with 2N relative DNA content in FIG. 10C reflects the known production of non-cycling progeny cells produced by the asymmetric self-renewal Lig-8 cells. In FIG. 10D, hair follicle cells show a similar DNA content profile, consistent with a large fraction of asymmetrically self-renewing adult stem cells.

DETAILED DESCRIPTION OF THE INVENTION

We have now discovered methods for propagating somatic hair follicle stem cells and melanocyte stem cells by conditionally suppressing asymmetric cell kinetics in the explanted hair follicle stem cells. This is accomplished by enhancing guanine nucleotide biosynthesis, thereby expanding guanine ribonucleotide pools. The methods of the invention include pharmacological methods and genetic methods. Somatic hair follicle stem cells can be used for a variety of applications including, but not limited to, cell replacement therapies such as hair transplants, gene therapies, tissue engineering of such as artificial skin and skin graft technology.

As used herein, somatic hair follicle stem cells derived from adult tissues are sometimes referred to as somatic stem cells or hair follicle stem cells or simply as stem cells. Somatic hair follicle stem cells include any stem cell isolated from the hair follicle. As used herein a stem cell is multi-potent and can give rise to a number of different cells, in contrast to differentiated cells. These include, but are not limited to, the multi-potent stem cell that gives rise to at least four different epidermal structures, the hair shaft, sebaceous glands, sweat glands, and epidermal keratinocytes (skin cells) and melanocyte stem cells responsible for producing melanocytes that produce melanin and put pigment into the hair shaft.

Figure 1A:
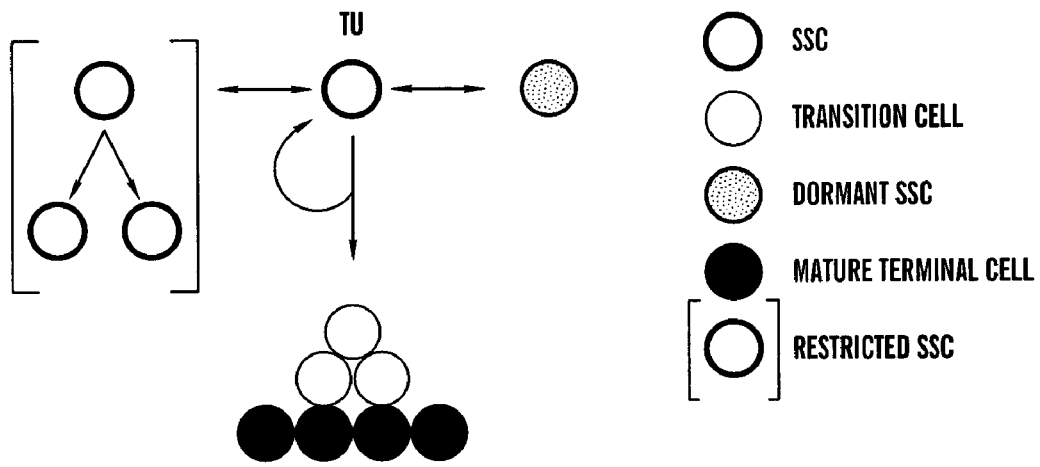
FIGS. 1A-1B depict the in vivo asymmetric kinetics of somatic stem cells.
Figure 1B:
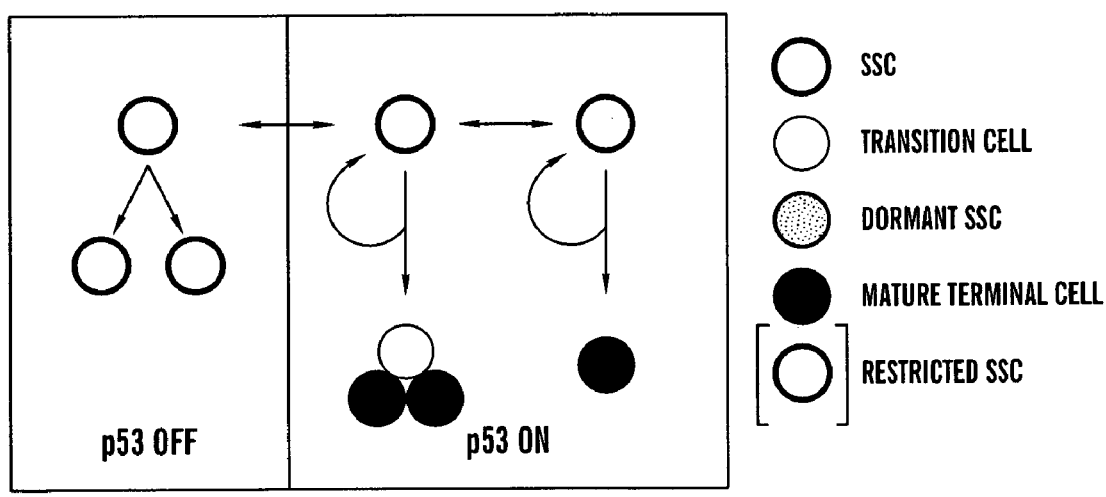

Adult somatic stem cells predominantly divide by asymmetric cell kinetics (see FIG. 1). While somatic stem cells also undergo limited symmetric divisions (that produce two identical stem cells) in developing adult tissues, such symmetric kinetics are restricted to periods of tissue expansion and tissue repair. Inappropriate symmetric somatic stem cell divisions evoke mechanisms leading to apoptosis of duplicitous stem cells (Potten and Grant, 1998). Some stem cells may also lie dormant for long periods before initiating division in response to specific developmental cues, as in reproductive tissues like the breast. However, the predominant cell kinetics state of somatic stem cells is asymmetric (Cairns, 1975; Poldosky, 1993; Loeffler and Potten, 1997).

During asymmetric cell kinetics, one daughter cell divides with the same kinetics as its stem cell parent, while the second daughter gives rise to a differentiating non-dividing cell lineage. The second daughter may differentiate immediately; or depending on the tissue, it may undergo a finite number of successive symmetric divisions to give rise to a larger pool of differentiating cells. The second daughter and its dividing progeny are called transit cells (Loeffler and Potten, 1997). Transit cell divisions ultimately result in mature, differentiated, terminally arrested cells. In tissues with high rates of cell turnover, the endpoint for differentiated terminal cells is programmed cell death by apoptosis.

Asymmetric cell kinetics evolved in vertebrates as a mechanism to insure tissue cell renewal while maintaining a limited set of stem cells and constant adult body mass. Mutations that disrupt asymmetric cell kinetics are an absolute requirement for the formation of a clinically significant tumor mass (Cairns, 1975). In many ways, asymmetric cell kinetics provide a critical protective mechanism against the emergence of neoplastic growths that are life threatening.

Figure 2:
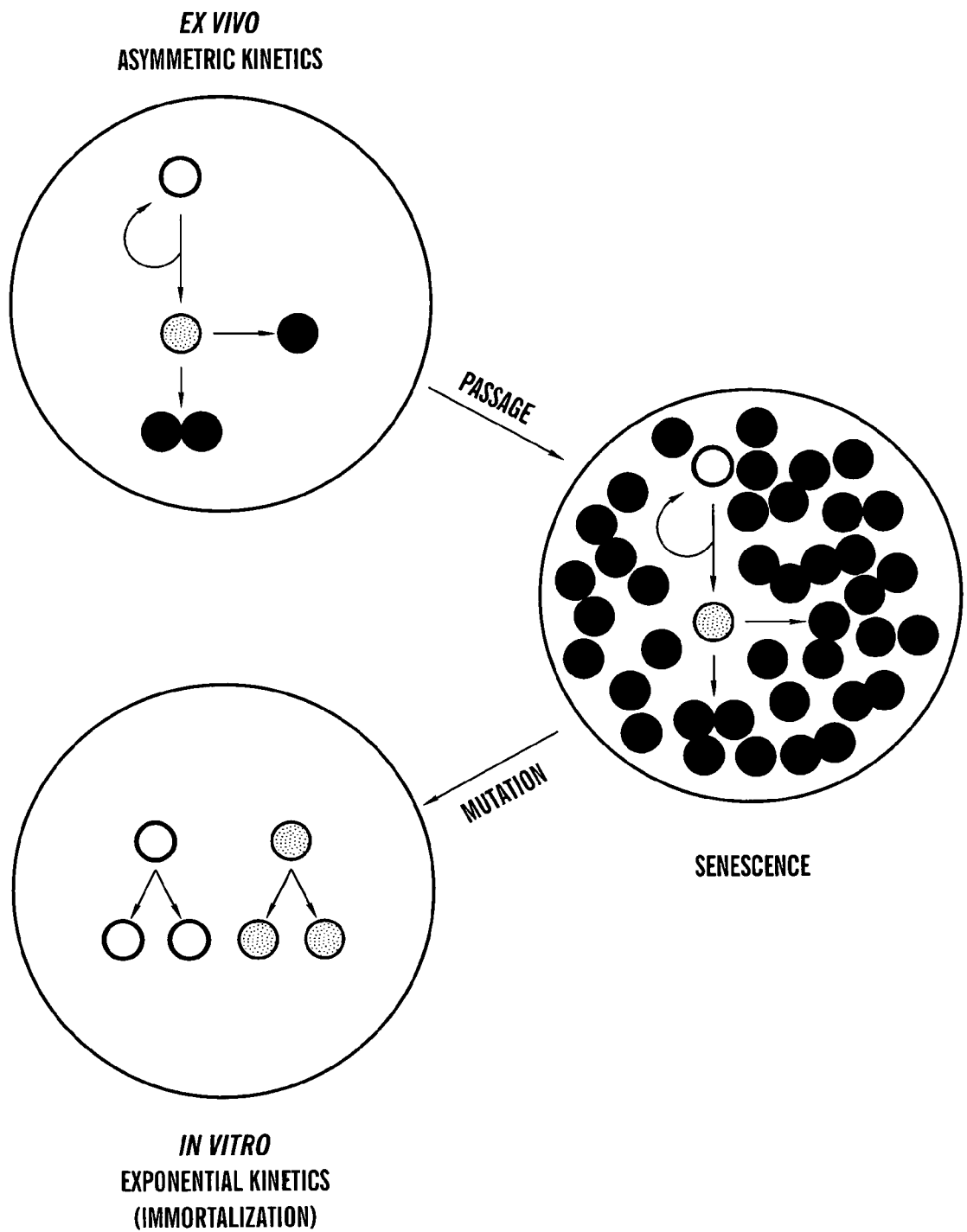
FIG. 2 depicts a cell kinetics barrier to the expansion of somatic stem cells in vitro. Of explanted tissue cells, somatic stem cells (bold-lined, open circles) have the capacity for long-term division ex vivo. However, if they retain even a rudimentary form of their in vivo asymmetric cell kinetics program, in vitro, their numbers will not increase. Instead, they will be diluted by the continuous accumulation of cells in terminal arrest lineages (closed circles). Continuous passage of cultures will result in "senescence" as a kinetics endpoint. In order to establish an immortal cell line, mutations must occur that either interfere with the maturation of terminal cells (immature terminal cells, thin-lined open circles) or that convert stem cells to symmetric exponential kinetics, in which only stem cells are produced. If asymmetric stem cell kinetics were suppressed, this model predicts that stem cells could be expanded in culture with fewer growth-activating mutations, like p53 mutations. P53 mutations relieve repression of IMPDH expression.

In culture, continued asymmetric cell kinetics of explanted cells are a major obstacle to their expansion in vitro (FIG. 2). Ongoing asymmetric kinetics results in dilution and loss of an initial relatively fixed number of stem cells by the accumulation of much greater numbers of their terminally differentiating progeny. If a sample includes both exponentially growing cells as well as somatic stem cells, the growth of the exponentially growing cells will rapidly overwhelm the somatic stem cells, leading to their dilution.

One regulator of asymmetric cell kinetics is the p53 tumor suppressor protein. Several stable cultured murine cell lines have been derived that exhibit asymmetric cell kinetics in response to controlled expression of the wild-type murine p53 (FIG. 1 B). (Sherley, 1991; Sherley et al, 1995 A-B; Liu et al., 1998 A-B; Rambhatla et al., 2001).

The p53 model cell lines have been used to define cellular mechanisms that regulate asymmetric cell kinetics. In addition to p53, the rate-limiting enzyme of guanine nucleotide biosynthesis, inosine-5'-monophosphate dehydrogenase (IMPDH) is an important determinant of asymmetric cell kinetics. IMPDH catalyzes the conversion of IMP to xanthosine monophosphate (XMP) for guanine nucleotide biosynthesis. This enzymatic reaction is rate-determining for the formation of the next metabolite in the pathway, GMP, from which all other cellular guanine nucleotides are derived.

Accordingly, high levels of GNPs promote exponential kinetics, whereas low levels of GNPs promote asymmetric cell kinetics. The present invention provides methods for expanding somatic hair follicle stem cells or melanocyte stem cells ex vivo by enhancing guanine nucleotide biosynthesis, thereby expanding cellular pools of GNPs and conditionally suppressing asymmetric cell kinetics.

According to methods of the invention, expansion of the human multi-potent somatic hair follicle stem cells can start with only a single cell. Preferably, one can start with a composition containing only 1% human multi-potent somatic hair follicle stem cells. These multi-potent human hair follicle stem cells can be enriched up to at least 30%, for example at least 40%, 50%, 60%, 70%, 80%, 90%, 95% of the entire composition because of the suppression of asymmetric cell kinetics.

Mechanisms which function downstream of the GNPs to regulate cell kinetics (i.e. asymmetric v. symmetric) can also be used to conditionally suppress asymmetric cell kinetics thereby effectively permitting a greater percent of expression by the stem cell. These mechanisms include both genetic and/or pharmacological approaches, analogous to those described in detail herein. For example, one can enhance expression of a protein downstream of the GNP biosynthesis pathway, if that protein inhibits asymmetric cell kinetics. Alternatively, one can downregulate expression of a protein downstream of the GNP pathway if it promotes asymmetric cell kinetics.

Pharmacological Methods for Stem Cell Expansion

In the pharmacological method of the present invention, somatic hair follicle stem cells or melanocyte stem cells are cultivated in the presence of compounds which enhance guanine nucleotide biosynthesis. This expands guanine nucleotide pools, which in turn suppress the undesired asymmetric cell kinetics thereby permitting expansion of stem cells resulting in production of a greater percent of stem cells. Preferably, the compounds are guanine nucleotide precursors (rGNPrs). More preferably, the rGNPr xanthosine (Xs), xanthine (Xn) or hypoxanthine (Hx). More preferably the rGNPr xanthosine or hypoxanthine. Even more preferably, the rGNPr is xanthine. These compounds can be used at effective concentrations ranging from 1 uM to 5 mM. Preferably the concentration ranges from 1 uM to 1 mM. More preferably the concentration is in the range of 50 uM to 1500 uM. One skilled in the art can determine the effective concentration necessary to suppress asymmetric kinetics of the hair follicle stem cell to be propagated.

Genetic Methods for Hair Follicle Stem Cell Expansion

In one embodiment of the invention, genes that lead to constitutive upregulation of guanine ribonucleotides (rGNPs) are introduced into the somatic hair follicle stem cells. Preferred genes are those that encode inosine-5'monophosphate dehydrogenase (IMPDH) or xanthine phosphoribosyltransferase (XPRT), or other genes which have the same biochemical effect. More preferably, the gene is XPRT. While there are currently no known mammalian forms of XPRT, and its substrate xanthine is present in very low levels in mammalian cells, the activity of the transgenic XPRT can be regulated by supplying xanthine exogenously. As explained below, it is preferred that the genes are operably linked to an inducible promoter.

In another embodiment of the invention, transgenic animals are generated with introduced genes that lead to constitutive upregulation of rGNPs. Methods for making transgenic animals are well known to those skilled in the art and any such method can be used.

In one preferred embodiment, the transgene introduced into the animal is the gene encoding for xanthine phosphoribosyltransferase (XPRT), for example from the protozoan *Leishmania donovani*. The XPRT enzyme can convert xanthine into xanthosine monophosphate, the critical precursor for cellular guanine nucleotides. This enzyme has no mammalian counterpart and its substrate can enter the cell via ubiquitously expressed nucleobase transporters. Therefore, one can control the kinetics of adult stem cells expressing XPRT that are derived from the transgenic animal by supplementing with or depriving the culture medium of xanthine. In the presence of xanthine, XPRT-expressing cells increase their cellular level of guanine nucleotides independently of their normal endogenous pathway involving the conversion of inosine monophosphate to xanthosaine monophosphate by the enzyme inosine monophosphate dehydrogenase. Preferably, the transgene is operably linked to an inducible promoter.

As used herein, the introduction of DNA into a host cell is referred to as transduction, sometimes also known as transfection or infection. Stem cells can be transduced ex vivo at high efficiency.

As used herein, the terms "transgene", "heterologous gene", "exogenous genetic material", "exogenous gene" and "nucleotide sequence encoding the gene" are used interchangeably and meant to refer to genomic DNA, cDNA, synthetic DNA and RNA, mRNA and antisense DNA and RNA, and sRNAs, miRNAs and RNAi's, which are introduced into the stem cell. The exogenous genetic material may be heterologous or an additional copy or copies of genetic material normally found in the individual or animal. When cells are to be used as a component of a pharmaceutical composition in a method for treating human diseases, conditions or disorders, the exogenous genetic material that is used to transform the cells may also encode proteins selected as therapeutics used to treat the individual and/or to make the cells more amenable to transplantation.

An expression cassette can be created for expression of the gene that leads to constitutive upregulation of guanine ribonucleotides. Such an expression cassette can include regulatory elements such as a promoter, an initiation codon, a stop codon, and a polyadenylation signal. It is necessary that these elements be operable in the stem cells or in cells that arise from the stem cells after infusion into an individual. Moreover, it is necessary that these elements be operably linked to the nucleotide sequence that encodes the protein such that the nucleotide sequence can be expressed in the stem cells and thus the protein can be produced. Initiation codons and stop codons are generally considered to be part of a nucleotide sequence that encodes the protein.

A variety of promoters can be used for expression of the transgene. Promoters that can be used to express the gene are well known in the art. Promoters include cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter and the herpes simplex tk virus promoter. For example, one can use a tissue specific promoter, i.e. a promoter that functions in some tissues but not in others. Such promoters include EF2 responsive promoters, etc. Regulatable promoters are preferred. Such systems include those using the lac repressor from *E. coli* as a transcription modulator to regulate transcription from lac operator-bearing mammalian cell promoters (Brown, M. et al., *Cell,* 49:603-612 (1987)), those using the tetracycline repressor (tetR) (Gossen, M., and Bujard, H., *Proc. Natl. Acad. Sci. USA* 89:5547-5551 (1992); Yao, F. et al., *Human Gene Therapy,* 9:1939-1950 (1998); Shockelt, P., et al., *Proc. Natl. Acad. Sci. USA,* 92:6522-6526 (1995)). Other systems include FK506 dimer, VP16 or p65 using astradiol, RU486, diphenol murislerone or rapamycin. Inducible systems are available from Invitrogen, Clontech and Ariad. Systems using a repressor with the operon are preferred. Regulation of transgene expression in target cells represents a critical aspect of gene therapy. For example, the lac repressor from *Escherichia coli* can function as a transcriptional modulator to regulate transcription from lac operator-bearing mammalian cell promoters (M. Brown et al., *Cell,* 49:603-612 (1987)); Gossen and Bujard (1992); (M. Gossen et al., *Natl. Acad. Sci. USA,* 89:5547-5551 (1992)) combined the tetracycline repressor (tetR) with the transcription activator (VP 16) to create a tetR-mammalian cell transcription activator fusion protein, tTa (tetR-VP16), with the tetO-bearing minimal promoter derived from the human cytomegalovirus (hCMV) major immediate-early promoter to create a tetR-tet operator system to control gene expression in mammalian cells. Recently Yao and colleagues (F. Yao et al., Hum Gene Ther. September 1;9(13):1939-50 (1998)). demonstrated that the tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter. One particular advantage of this tetracycline inducible switch is that it does not require the use of a tetracycline repressor-mammalian cells transactivator or repressor fusion protein, which in some instances can be toxic to cells (M. Gossen et al., *Natl. Acad. Sci. USA,* 89:5547-5551 (1992); P. Shockett et al., *Proc. Natl. Acad. Sci. USA,* 92:6522-6526 (1995)), to achieve its regulatable effects.

The effectiveness of some inducible promoters increases over time. In such cases one can enhance the effectiveness of such systems by inserting multiple repressors in tandem, e.g. TetR linked to a TetR by an IRES. Alternatively, one can wait at least 3 days before screening for the desired function. While some silencing may occur, it is minimized given the large number of cells being used, preferably at least $1\times10^4$, more preferably at least $1\times10^5$, still more preferably at least $1\times10^6$, and even more preferably at least $1\times10^7$, the effect of silencing is minimal. One can enhance expression of desired proteins by known means to enhance the effectiveness of this system. For example, using the Woodchuck Hepatitis Virus Posttranscriptional Regulatory Element (WPRE). See Loeb, V. E., et al., *Human Gene Therapy* 10:2295-2305 (1999); Zufferey, R., et al., *J. of Virol.* 73:2886-2892 (1999); Donello, J. E., et al., *J. of Virol.* 72:5085-5092 (1998).

Examples of polyadenylation signals useful to practice the present invention include but are not limited to human collagen I polyadenylation signal, human collagen II polyadenylation signal, and SV40 polyadenylation signal.

In order to maximize protein production, codons may be selected which are most efficiently translated in the cell. The skilled artisan can prepare such sequences using known techniques based upon the present disclosure.

The exogenous genetic material that includes the transgene operably linked to the regulatory elements may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA, which can integrate into the chromosome, may be introduced into the cell. When introducing DNA into the cell, reagents, which promote DNA integration into chromosomes, may be added. DNA sequences, which are useful to promote integration, may also be included in the DNA molecule. Alternatively, RNA may be introduced into the cell.

Selectable markers can be used to monitor uptake of the desired gene. These marker genes can be under the control of any promoter or an inducible promoter. These are well known in the art and include genes that change the sensitivity of a cell to a stimulus such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, LacZ, nerve growth factor receptor (NGFR), etc.

For example, one can set up systems to screen hair follicle stem cells automatically for the marker. In this way one can rapidly select transduced hair follicle stem cells from non-transformed cells. For example, the resultant particles can be contacted with about one million cells. Even at transduction rates of 10-15% one will obtain 100-150,000 cells. An automatic sorter that screens and selects cells displaying the marker, e.g. GFP, can be used in the present method.

When the transgene is XPRT, cells expressing XPRT will be resistant to cytotoxic IMPDH inhibitors such as mycophenolic acid in the presence of xanthine. Thus, transduced hair follicle stem cells can be selected from non-transformed cells by culturing transfectants in the presence of an IMPDH inhibitor (such as mycophenolic acid) and xanthine. One can use other markers to readily select transduced cells.

Vectors include chemical conjugates, plasmids, phage, etc. The vectors can be chromosomal, non-chromosomal or synthetic. Commercial expression vectors are well known in the art, for example pcDNA 3. 1, pcDNA4 HisMax, pACH, pMT4, PND, etc. Preferred vectors include viral vectors, fusion proteins and chemical conjugates. Retroviral vectors include Moloney murine leukemia viruses and pseudotyped lentiviral vectors such as FIV or HIV cores with a heterologous envelope. Other vectors include pox vectors such as orthopox or avipox vectors, herpesvirus vectors such as a herpes simplex I virus (HSV) vector (Geller, A. I. et al., (1995), *J. Neurochem,* 64: 487; Lim, F., et al., (1995) in *DNA Cloning: Mammalian Systems,* D. Glover, Ed., Oxford Univ. Press, Oxford England; Geller, A. I. et al. (1993), *Proc Natl. Acad. Sci.: U.S.A.* 90:7603; Geller, A. I., et al., (1990) *Proc Natl. Acad. Sci USA* 87:1149), adenovirus vectors (LeGal LaSalle et al. (1993), *Science,* 259:988; Davidson, et al. (1993) *Nat. Genet* 3: 219; Yang, et al., (1995) *J. Virol.* 69: 2004) and adeno-associated virus vectors (Kaplitt, M. G., et al. (1994) *Nat. Genet.* 8: 148).

The introduction of the gene into the stem cell can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors, adjuvant-assisted DNA, gene gun, catheters, etc.

The vectors are used to transduce the hair follicle stem cells ex vivo. One can rapidly select the transduced cells by screening for the marker. Thereafter, one can take the transduced cells and grow them under the appropriate conditions or insert those cells into a host animal.

In one embodiment, one can use a composition for topical administration containing the rGNPr as the active ingredient. The composition includes a topical carrier. Such carriers are well known in the art and selected to provide the composition in the desired form, e.g., as a liquid, lotion, cream, paste, gel, powder or ointment and may be comprised of a material of either naturally occurring or synthetic origin. Examples include water, alcohols and other non-toxic organic solvents, glycerin, mineral oil, silicone, petroleum jelly, lanolin, fatty acids, vegetable oils, parabens, waxes and the like. In one preferred embodiment the composition may be administered in the form of a shampoo.

Somatic Hair Follicle Stem Cells

The hair follicle stem cells and the melanocyte stem cells of the present invention may be isolated from tissue of an adult mammal, preferably a human. The cells include but are not limited to, melanocyte stem cells responsible for producing melanocytes that put pigment into the hair shaft and the multi-potent hair follicle stem cell that gives rise to different epidermal structures, e.g. the hair shaft, sebaceous glands, sweat glands, and epidermal keratinocytes. Different hair follicle stem cells can be isolated from other cells by means known in the art. Melanocytes can be readily identified from other cells. For example, melanocytes contain microphthalmia transcription factor. Although the multi-potent stem cell that gives rise to the hair shaft, sebaceous glands, sweat glands, and epidermal keratinocytes is exemplified herein, the methods of ex vivo propagation described herein can be applied to any hair follicle stem cell whether it be muti-potent, pluripotent, or a unique progenitor subtype, such as a stem cell that produces only sebaceous glands and not, for example, sweat glands.

The somatic hair follicle stem cells act as precursor cells, which produce daughter cells that mature into differentiated hair follicle cells. The hair follicle stem cells can be isolated from the individual in need of hair follicle stem cell therapy, or from another individual. Preferably, the individual is a matched individual to insure that rejection problems do not occur. Those having ordinary skill in the art can readily identify matched donors using standard techniques and criteria. Other therapies to avoid rejection of foreign cells are known in the art. For example, somatic hair follicle stem cells may be immune-privileged, so the graft versus host disease after allogenic transplant may be minimal or non-existent (Weissman, 2000). Hair follicle stem cells from a matched donor may be administered by any known means, for example, intravenous injection, or injection directly into the appropriate tissue, such as the skin on the scalp.

Cells can be obtained from donor tissue, such as donor skin or scalp, by dissociation of individual cells from the connecting extracellular matrix of the tissue. Tissue is removed using a sterile procedure, and the cells are dissociated using any method known in the art including treatment with enzymes such as trypsin, collagenase, and the like, or by using physical methods of dissociation such as with a blunt instrument.

In one preferred embodiment, intact hair follicles are dissected from the skin under sterile conditions. The hair shaft is then resected at its point of exit from the follicle. The intact follicle is then digested with enzymes, repeatedly washed, and filtered with a nylon mesh to remove external cells (e.g., dermal fibroblasts) that adhere to the follicle capsule. The follicle is then opened with a single longitudinal incision and placed in culture medium.

Any medium can be used that is capable of supporting cell growth, including HEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. Serum can contain xanthine, hypoxanthine, or other compounds which enhance guanine nucleotide biosynthesis, although generally at levels below the effective concentration to suppress asymmetric cell kinetics. Thus, preferably a defined, serum-free culture medium is used, as serum contains unknown components (i.e. is undefined). Preferably, if serum is used, it has been dialyzed to remove rGNPrs. A defined culture medium is also preferred if the cells are to be used for transplantation purposes. A particularly preferable culture medium is a defined culture medium comprising a mixture of DMEM, F 12, and a defined hormone and salt mixture. As indicated herein, by including a compound such as a rGNPr, asymmetric cell kinetics are suppressed. Thus, the effect of division by differentiated transit cells, which results in the diluting of the hair follicle stem cells, is reduced.

The culture medium can be supplemented with a proliferation-inducing growth factor(s). As used herein, the term "growth factor" refers to a protein, peptide or other molecule having a growth, proliferative, differentiative, or trophic effect on stem cell. Growth factors that may be used include any trophic factor that allows hair follicle stem cells to proliferate, including any molecule that binds to a receptor on the surface of the cell to exert a trophic, or growth-inducing effect on the cell. Preferred proliferation-inducing growth factors include EGF, amphiregulin, acidic fibroblast growth factor (aFGF or FGF-1), basic fibroblast growth factor (bFGF or FGF-2), transforming growth factor alpha (TGF.alpha.), and combinations thereof. Growth factors are usually added to the culture medium at concentrations ranging between about 1 fg/ml to 1 mg/ml. Concentrations between about 1 to 100 ng/ml are usually sufficient. Simple titration experiments can be easily performed to determine the optimal concentration of a particular growth factor. In one preferred embodiment, Epidermal growth factor is used.

In addition to proliferation-inducing growth factors, other growth factors may be added to the culture medium that influence proliferation and differentiation of the cells including NGF, platelet-derived growth factor (PDGF), thyrotropin releasing hormone (TRH), transforming growth factor betas (TGFβs), insulin-like growth factor (IGF-1) and the like. Differentiation can also be induced by growing cells to confluency.

Hair follicle stem cells can be cultured in suspension or on a fixed substrate. For example, the stem cells can be grown on a hydrogel, such as a peptide hydrogel, as described below. Alternatively, the stem cells can be propagated on tissue culture plates or in suspension cultures. Cell suspensions can be seeded in any receptacle capable of sustaining cells, particularly culture flasks, cultures plates, or roller bottles, more particularly in small culture flasks such as 25 cm2 cultures flasks. Preferably, the hair follicle stem cells are grown on tissue culture plates. In one preferred embodiment, cells are cultured at high cell density to promote the suppression of asymmetric cell kinetics.

Conditions for culturing should be close to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 350 C to about 37° C.

Cells are preferably cultured for 3-30 days, preferably at least about 7 days, more preferably at least 10 days, still more preferably at least about 14 days. Cells can be cultured substantially longer. They can also be frozen using known methods such as cryopreservation, and thawed and used as needed.

Another preferred embodiment provides for deriving clonal lines of somatic hair follicle stem cells by limiting dilution plating or single cell sorting. Methods for deriving clonal cell lines are well known in the art and are described for example in Puck et al., 1956; Nias et al., 1965; and Leong et al., 1985.

Uses of Expanded Somatic Hair Follicle Stem Cells

The present invention also provides for the administration of expanded populations of hair follicle stem cells and melanocyte stem cells to a patient in need thereof. The term "administration" as used herein refers to well recognized forms of administration, such as intravenous or injection, as well as to administration by transplantation, for example transplantation of intact hair follicle cells containing transplanted hair follicle stem cells, or transplantation of skin grafts containing transplanted hair follicle stem cells or transplantation of tissue engineered skin derived from hair follicle stem cells.

The expanded hair follicle stem cells of the present invention can be used for a variety of purposes, including, but not limited, to hair transplant therapy, such as transplantation of hair follicles or skin grafts containing transplanted stem cells into the scalp or skin; tissue engineering applications, such as their use in generation of functional artificial skin or functional skin grafts; and in gene therapy applications.

The expanded hair follicle stem cells of the invention are also particularly useful for facilitating research on hair follicle stem cell biology and differentiation.

In one preferred embodiment, autologous hair follicle stem cells are used to replace injured hair follicle cells and produce functional tissue engineered skin and skin grafts. The use of autologous hair follicle stem cells reduces the need for immune suppression interventions upon transplant. One can also administer topical compositions containing the rGNPr to an individual to stimulate production of the desired stem cells.

One can administer the hair follicle stem cells and optionally melanocyte stem cells to individuals desiring hair transplants in the same manner conventional hair transplants use.

Transplantation of tissue engineered artificial skin or skin grafts with newly introduced hair follicle stem cells, is particularly useful for treatment of injured skin, such as found in burn victims. Recent developments in artificial skin engineering have yielded an artificial dermis that can be used for skin grafting. However, the benefits of such a skin graft are limited, as it is unable to fully restore the abilities of real skin to secrete desiccation-resistant oils and sweat for thermo-regulation. The limitations can be resolved through the utilization of hair follicle stem cells. Hair follicle stem cells are responsible for the generation of skin accessory organs such as sebaceous glands as well as hair follicles. Therefore, the use of hair follicle stem cells in engineering skin can bridge the gap between artificial and natural skin.

Methods for generation of artificial skin are known in the art. See, for example, U.S. Pat. Nos. 4,489,304, 6,733,530, 5,800,811 and 6,689,608, which are herein incorporated by reference in their entirety.

For engineering of artificial skin, the ex vivo propagated hair follicle stem cells of the invention can be mixed with other cells, such as cultured keratinocytes, fibroblasts, and mesenchymal stem cells, as described in U.S. Pat. Nos. 5,800, 811 and 5,489,304.

In one preferred embodiment because hair follicle stem cells differentiate into keratinocytes, hair, sweat glands and sebaceous glands, the hair follicle stem cells can be used in isolation for the generation of artificial skin. In one preferred embodiment, autologous cells are used in the generation of artificial skin.

Propagated hair follicle stem cells can also be used in skin regeneration and wound healing strategies. For example, matrices such as those described in U.S. Pat. No. 4,060,081, the teachings of which are incorporated herein by reference in its entirety, can be seeded with hair follicle stem cells to ensure proper formation of functional skin.

In one preferred embodiment, individual hair follicle stem cells can be introduced into the skin or scalp by injection.

Hair follicle stem cells are particularly useful for treating hair loss, such as caused by male pattern baldness or alopecia. Individual hair follicles, where hair follicle stem cells have been introduced can be transplanted, by surgical means, into the skin or scalp of an individual. As such, hair loss is combated by the ability of the hair follicle stem cells to produce hair. For example, transplantation of hair follicles into the scalp, or into or into skin grafts would effectively increase the number of functional hair follicles in balding individuals. Such transplantation could complement or replace follicular unit transplantation (FIT), the current means of hair restoration.

Gene Therapy Applications

According to the invention, in addition to the introduction of genes that lead to constitutive upregulation of guanine ribonucleotides, the somatic hair follicle stem cells or melanocyte stem cells, preferably the hair follicle stem cells, can be further genetically altered prior to reintroducing the cells into the individual for gene therapy, to introduce a gene whose expression has therapeutic effect on the individual.

For example, the hair follicle cells may have a defective gene that inhibits hair growth. By introducing normal genes in expressible form, individuals suffering from such a deficiency can be provided the means to compensate for genetic defects and eliminate, alleviate or reduce some or all of the symptoms of the deficiency.

A vector can be used for expression of the transgene encoding a desired wild type hormone or a gene encoding a desired mutant hormone. Preferably, as described above, the transgene is operably linked to regulatory sequences required to achieve expression of the gene in for example the hair follicle stem cell or the cells that arise from the hair follicle stem cells after they are infused into an individual. Such regulatory sequences include a promoter and a polyadenylation signal. The vector can contain any additional features compatible with expression in stem cells or their progeny, including for example selectable markers.

Administration of Expanded Somatic Hair Follicle Stem Cells

The methods of the invention involve administering the expanded hair follicle stem cells or melanocyte stem cells to an individual by standard means, such as intravenous infusion and mucosal injection, as well as administration to an individual by transplantation. Transplantation techniques are well known to those skilled in the art and include surgical and skin grafting techniques.

In one preferred embodiment, hair follicle stem cells are introduced into an intact hair follicle present in the skin or scalp of an individual, or in a skin graft. Individual hair follicle stem cells can be introduced by injection. When regrowing hair, one preferably also co-administers melanocyte stem cells.

In another embodiment, the hair follicle stem cells are used to engineer skin either alone or in the presence of additional stem cell niche components, such as stromal cells and extracellular matrix. The newly engineered skin is then transplanted into an individual by surgical means.

The discovery that isolated stem cells may be expanded ex vivo and administered intravenously provides the means for systemic administration. In certain applications, such as gene therapeutic methods, systemic administration by intravenous infusion may be desired. In a preferred embodiment, the stem cells are administered to an individual by infusion into the superior mesenteric artery or celiac artery. The stem cells may also be delivered locally by irrigation down the recipient's airway or by direct injection into the mucosa of the intestine.

After isolating the hair follicle stem cells, the cells can be administered after a period of time sufficient to allow them to convert from asymmetric cell kinetics to exponential kinetics, typically after they have been cultured from 1 day to over a year. Preferably the cells are cultured for 3-30 days, more preferably 4-14 days, most preferably at least 7 days.

In one embodiment of the invention, the stem cells can be induced to differentiate following expansion in vitro, prior to administration to the individual. Preferably, the pool of guanine ribonucleotides is decreased at the same time differentiation is induced, for example by removal of the rGNPr from the culture medium (if a pharmacological approach has been used) or by downregulating expression of the transgene.

Differentiation of the hair follicle stem cells can be induced by any method known in the art which activates the cascade of biological events which lead to growth, which include the liberation of inositol triphosphate and intracellular $Ca^{2+}$, liberation of diacyl glycerol and the activation of protein kinase C and other cellular kinases, and the like. Treatment with phorbol esters, differentiation-inducing growth factors and other chemical signals can induce differentiation. Differentiation can also be induced by plating the cells on a fixed substrate such as flasks, plates, or coverslips coated with an ionically charged surface such as poly-L-lysine and poly-L-ornithine and the like.

Other substrates may be used to induce differentiation such as collagen, fibronectin, laminin, MATRIGEL™ (Collaborative Research), and the like. Differentiation can also be induced by leaving the cells in suspension in the presence of a proliferation-inducing growth factor, without reinitiation of proliferation.

Differentiation can be determined using immunocytochemistry techniques well known in the art. Immunocytochemistry (e.g. dual-label immunofluorescence and immunoperoxidase methods) utilizes antibodies that detect cell proteins to distinguish the cellular characteristics or phenotypic properties of differentiated cell types compared to markers present on hair follicle stem cells.

For intravenous administration of hair follicle stem cells, the isolated hair follicle stem cells are removed from culture dishes, washed with saline, centrifuged to a pellet and resuspended in a glucose solution which is infused into the patient. Between $10^4$ and $10^{13}$ cells per 100 kg person are administered per infusion. Preferably, between about $1-5 \times 10^4$ and $1-5 \times 10^7$ cells are infused intravenously per 100 kg person. More preferably, between about $1 \times 10^4$ and $5 \times 10^6$ cells are infused intravenously per 100 kg person. The cells can also be injected directly into the intestinal mucosa through an endoscope.

In some embodiments, a single administration of cells is provided. In other embodiments, multiple administrations are used. Multiple administrations can be provided over periodic time periods such as an initial treatment regime of 3-7 consecutive days, and then repeated at other times.

Another embodiment of the invention provides transgenic non-human animals into whose genome is stably integrated an exogenous DNA sequence comprising a constitutive promoter expressed in all cell types operably linked to a DNA sequence encoding a protein that leads to constitutive upregulation of guanine nucleotides, including the gene encoding inosine-5'-monophosphate dehydrogenase (IMPDH) or xanthine phophoribosyl transferase (XPRT). Preferably, the transgene is XPRT. Preferably, the transgenic animal is a mammal such as a mouse, rat or sheep.

The term "animal" here denotes all mammalian animals except humans. It also includes an individual animal in all stages of development, including embryonic and fetal stages. A"transgenic" animal is any animal containing cells that bear genetic information received, directly or indirectly, by deliberate genetic manipulation at the subcellular level, such as by microinjection or infection with recombinant virus.

"Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the invention also encompasses the use of extrachromosomally replicating DNA sequences, such as might be engineered into yeast artificial chromosomes.

The term "germ cell line transgenic animal" refers to a transgenic animal in which the genetic information has been taken up and incorporated into a germ line cell, therefore conferring the ability to transfer the information to offspring. If such offspring, in fact, possess some or all of that information, then they, too, are transgenic animals.

The information to be introduced into the animal is preferably foreign to the species of animal to which the recipient belongs (i.e., "heterologous"), but the information may also be foreign only to the particular individual recipient, or genetic information already possessed by the recipient. In the last case, the introduced gene may be differently expressed than is the native gene.

The transgenic animals of this invention are other than human, and produce milk, blood serum, and urine. Farm animals (pigs, goats, sheep, cows, horses, rabbits and the like), rodents (such as mice), and domestic pets (for example, cats and dogs) are included in the scope of this invention. One preferred animal is a mouse. Mouse strains which are suitable for the derivation of transgenic mice as described herein are any common laboratory mouse strain. Preferred mouse strains to use for the derivation of transgenic mice founders of the present invention include FVB and C57 strains. Preferably, founder mice are bred onto wild-type mice to create lines of transgenic mice.

It is highly preferred that a transgenic animal of the present invention be produced by introducing into single cell embryos appropriate polynucleotides that encode XPRT or IMPDH, or fragments or modified products thereof, in a manner such that these polynucleotides are stably integrated into the DNA of germ line cells of the mature animal, and are inherited in normal mendelian fashion.

Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals. Those techniques as well known. See reviews of standard laboratory procedures for microinjection of heterologous DNAs into mammalian fertilized ova, including Hogan et al., Manipulating the mouse embryo, (Cold Spring Harbor Press 1986); Krimpenfort et al., Bio/Technology 9:844 (1991); Palmiter et al., Cell, 41: 343 (1985); Kraemer et al., Genetic manipulation of the early mammalian embryo, Cold Spring Harbor Laboratory Press 1985; Hammer et al., Nature, 315: 680 (1985); Wagner et al., U.S. Pat. No. 5,175,385; Krimpenfort et al., U.S. Pat. No. 5,175,384, the respective contents of which are incorporated by reference. See also U.S. Pat. Nos. 4,736,866, 5,387,742, 5,545,806, 5,487,992, 5,489,742, 5,530,177, 5,523,226, 5,489,743, 5,434,340, and 5,530,179.

In another embodiment of the invention, a method is provided for treating baldness. The method comprises administering to a subject a composition that stimulates conversion of hair follicle stem cells from asymmetric cell kinetics to symmetric cell kinetics resulting in enhanced proliferation of said hair follicle stem cells with a reversibly reduced production of differentiating progeny cells.

In one preferred embodiment, the agent that stimulates conversion of the stem cells from asymmetric cell kinetics to symmetric cell kinetics is a guanine nucleotide precursor (rGNPr), a analogue or derivative thereof, such as xanthosine, hypoxanthine, or xanthine. These agents can be used in the form of a hair product.

As used herein "baldness" refers to the loss of hair or its failure to grow on any portion of the scalp or skin and is not limited to the complete absence of hair.

The composition for treating baldness can be administered by any means known to those skilled in the art. In one embodiment the composition is administered topically. Alternatively, the hair product composition can be administered by any known means, such as injection, e.g. injection into the scalp.

The invention further provides for compositions comprising a population of human somatic hair follicle stem cells. Such compositions can comprise a population of cells from 10-100,000, or more, of somatic hair follicle stem cells. One can have any number of cells as part of the population including, but not limited to, 10, 20, 30, 40, 50, 100, 300, 500, 600, 800, 1,000 etc. cells in the composition.

In one embodiment, the composition is made up of at least 60% multi-potent somatic hair follicle stem cells. In another embodiment, the composition is at least 70%, at least 75%, at least 80%, at least 85%, at least 90%, at least 95% or at least 99% multi-potent somatic hair follicle stem cells.

A cell is multi-potent if it can still differentiate into at least two, preferably three other cells associated with hair follicle cells as described above. The multi-potency of cells can be determined by methods well known to those skilled in the art and by using methods as described herein.

EXAMPLES

Example 1

Propagation of Somatic Mouse Whisker Follicle Stem Cells

Purine nucleoside metabolites (i.e., rGNPrs) have been used as pharmacological agents to switch hair follicle stem cells from their default asymmetric cell kinetics program to symmetric kinetics. In mice, stem cells are thought to lie in the bulge region of the hair follicle. However, during the hair growth cycle, the cells are believed to migrate from the bulge region to a place at the base of the hair follicle known as the bulb (Fuchs, 2000). These migratory patterns and the general difficulty of dissecting these regions from hair follicles have foiled attempts to establish hair follicle stem cells lines. We have avoided these barriers by isolating intact mouse whisker hair follicles (methods of Kobayashi et al., 1993; Jahoda and Oliver, 1991), transecting them, and culturing outgrowth cells in the presence of three different agents, xanthosine (Xs), xanthine (Xn), and hypoxanthine (Hx). The purines Xn and Hx utilize distinct cellular enzymes to accomplish the same effect as Xs, increased production of guanine ribonucleotides.

Intact mouse whisker hair follicles were dissected from the skin under sterile conditions. The hair shaft was resected at its point of exit from the follicle. The intact follicle was then digested with trypsin, repeatedly washed, and filtered with a nylon mesh to remove external cells that adhere to the follicle capsule. The follicle was then opened with a single longitudinal incision and place in culture medium supplemented with 10% dialyzed fetal bovine serum, epidermal growth factor, and one of three different purine nucleoside metabolites (Hypoxyanthine, xanthosine, or xanthine) each supplemented to 400 uM.

Figure 3:
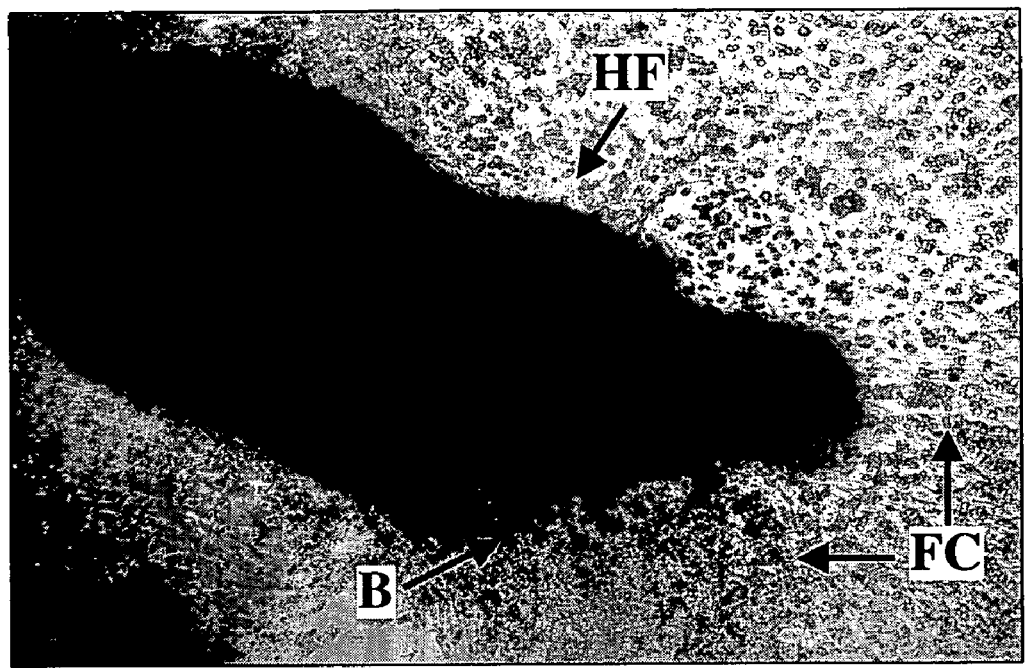
FIG. 3 shows the explosive outgrowth of hair follicle cells when rGNPrs are used for selection. Hair follicle (HF) in culture with stem cell multiplication technique applied. Bottom (B) of follicle's collagen capsule has burst open due to inability to contain rapidly multiplying hair follicle cells. Outgrowing follicle cells (FCs) are morphologically distinct from fibroblasts (F) seen in FIG. 4.
Figure 4:
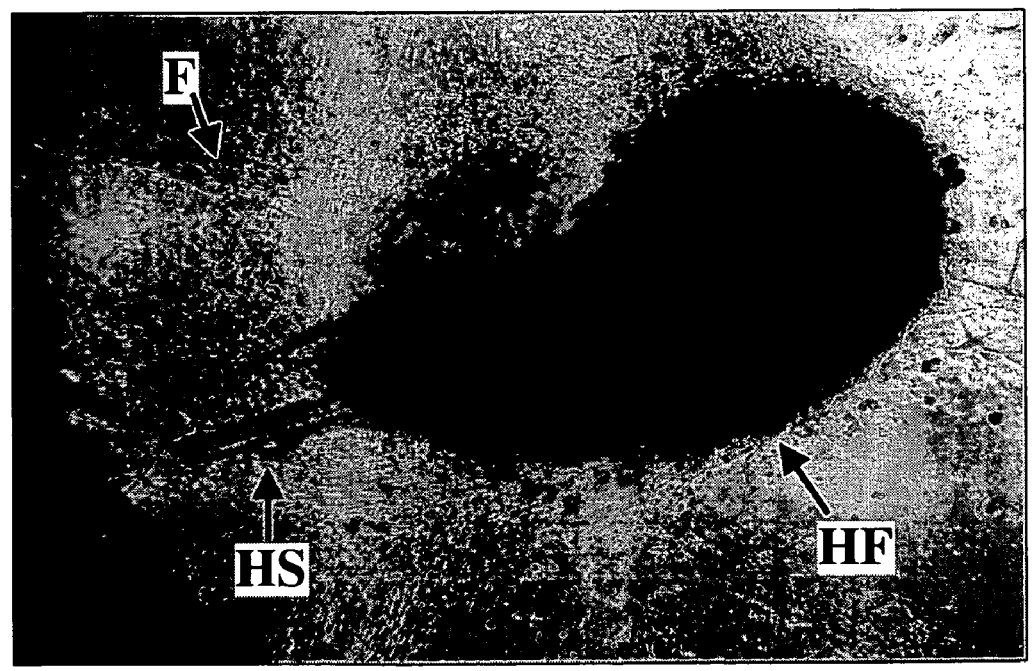
FIG. 4 shows the poor outgrowth of hair follicle cells when multiplication technique using rGNPrs is not employed. Hair follicle (HF) in culture with undesirable fibroblasts (F) growing from untreated outer surface. HS, hair-shaft exiting hair follicle.

Trypsinization and filtration to remove any cells adherent to the outer wall of hair follicles precluded dermal fibroblast growth, resulting in no fibroblasts from within the follicle itself (FIG. 3). Epithelial cells readily grew out in cultures of transected hair follicles supplemented with purine nucleoside precursors. This is in contrast to the poor outgrowth of hair follicle cells when protease treatment and purine nucleoside metabolites are not used (FIG. 4)

The first effect of the purine metabolites was noted when cell counts were performed on secondary cultures. Among all cultures starting with three transfected hair follicles in one well of a 24-well plate, those supplemented with Xn reached confluency first. Confluent primary cultures were transferred into to 25-cm$^2$ flasks. Seven days after this transfer, cell counts were performed before transferring cultures to 75-cm$^2$ flasks. At this time, cultures supplemented with Xn and Hx exhibited 5- to 6-fold more cells than those receiving no purine supplement or Xs did. Each purine nucleoside metabolite tested showed results consistent with shifting adult stem cells from asymmetric cell kinetics to symmetric cell kinetics.

After outgrowth of the follicle epithelial cells, cultures were trypsinized to harvest cells for secondary culture. Harvested cells were then plated by limiting dilution in 96 well plates in the presence or absence of the respective concentration of purine metabolite used for their initial outgrowth. In this manner, purine metabolite-dependent clonal expansion was verified. The results of these analyses are outline in Table 1. Only the Xn-supplemented culture yielded a significant number of cell clones with a marked dependence on Xn. Seventeen Xn-derived clones were transferred to 24-well plates, and 15 survived expansion to full scale cultures for cryo-preservation.

TABLE 1

Cell clone efficiency from purine-supplemented hair follicle epithelial cell cultures with and without purine-supplementation during cloning.

| Culture Supplement | Cloning Condition Purine-free (positive wells/ total wells) | Cloning Condition Purine-supplemented (positive wells/ total wells) |
|---|---|---|
| Control (no purine) | 0/96 | not done |
| Hx | 0/96 | 6/480 |
| Xs | 0/96 | 1/480 |
| Xn | 4/96 | 50/480 |

In this experiment, xanthine worked the best in promoting enhanced growth of mouse whisker follicle epithelial cells, suggesting a higher fraction of stem cells.

Figure 5:
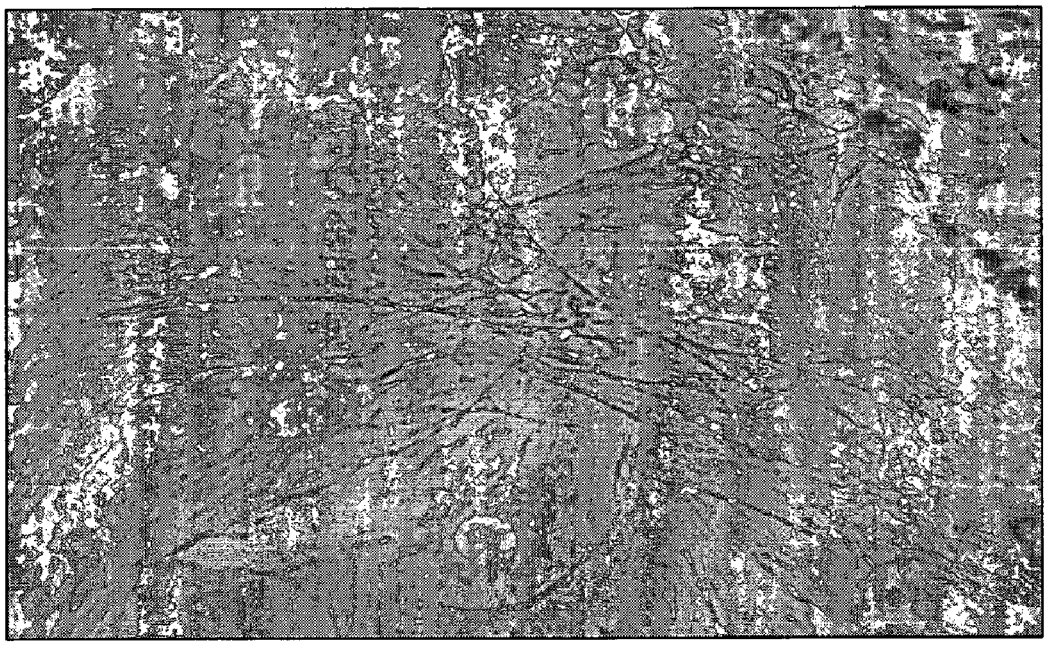
FIG. 5 shows a micrograph of undifferentiated hair follicle stem cell line 5B8. This is a representative micrograph of crystal violet-stain for one of several hair follicle stem cell lines prepared and cultured under non-differentiating conditions.
Figure 6:
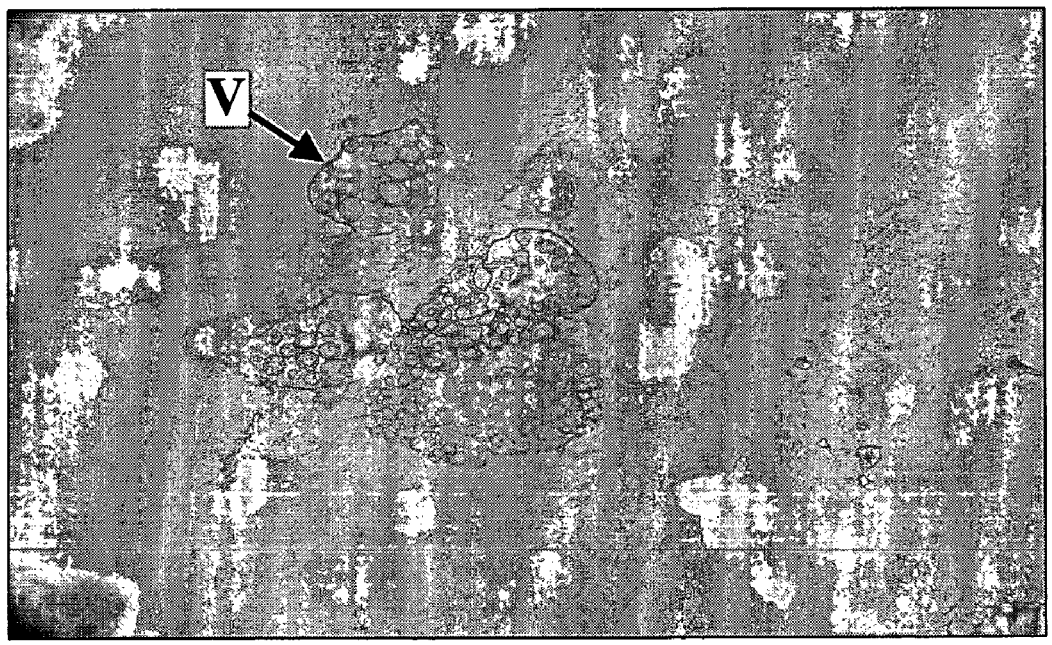
FIG. 6 shows the production of differentiated cell types by culturing hair follicle stem cell line 5B8 under differentiating conditions. Micrograph of crystal violet-stain for line 5B8 cells under conditions that promote cell differentiation. Differentiated cells contain vesicles (V) not present when grown under routine culture conditions. These vesicles also contain lipids, the chief byproduct of the skin's oil-producing accessory organ, the sebaceous gland. Thus, 5B8 cells have the ability to produce differentiated skin accessory organs, one of the principal properties of hair follicle stem cells.
Figure 7:
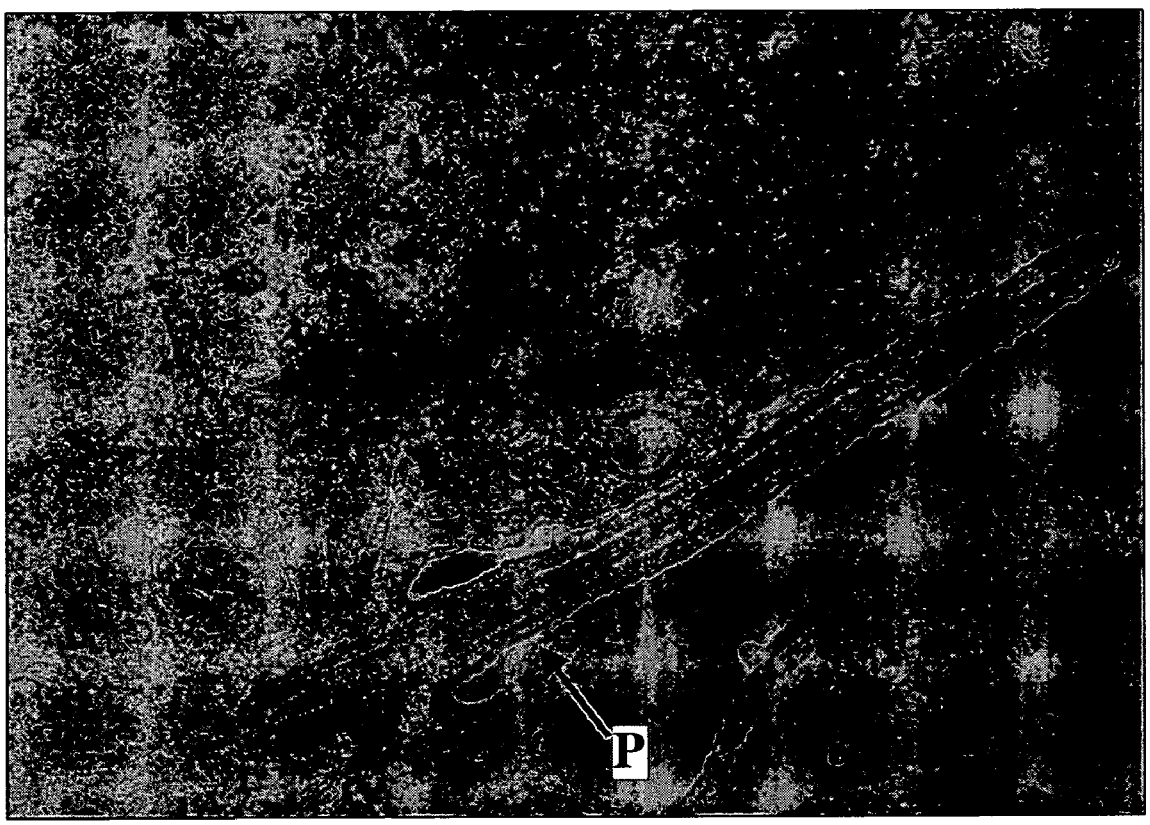
FIG. 7 shows a transmission electron microscopy (TEM) analysis of the ultrastructure of the putative hair follicle stem cell line 5B8. A transmission electron micrograph shows a primary cilium (P) that protrudes from the interior of a 5B8 cell. This analysis shows that this clonally-derived hair follicle cell line is capable of producing at least two types of differentiated cells, one characterized by primary cilium formation and the other by sebaceous differentiation (as shown in FIG. 6).

Several lines were obtained with properties indicative of hair follicle cells. For example, see FIG. 5 that shows an undifferentiated hair follicle stem cell line, 5B8, that has been cultured in non-differentiating conditions and stained with crystal violet indicating that the cell line remains undifferentiated. Under differentiating conditions, cells of line 5B8 differentiate into cells that contain lipids of sebaceous glands (FIG. 6). Transmission electron microscopy (TEM) analysis of the ultrastructure of hair follicle stem cell line 5B8 reveals that the cell line is capable of producing at least two types of differentiated cells, one characterized by sebaceous differentiation (FIG. 6) and one characterized by primary cilium formation (FIG. 7). It is expected that cell line 5B8 also has sweat production capacity. This will be confirmed when appropriate tests are developed to measure the trait.

Figure 8C:
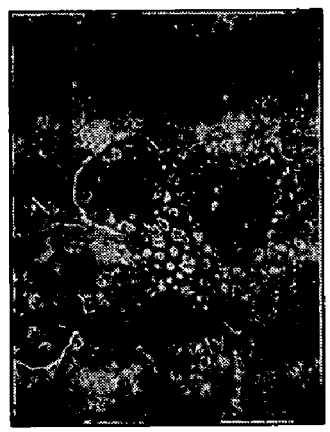
FIG. 8C, A higher magnification (400×) light micrograph shows vesicles in crystal-violet stained cells. Note that the differentiated cells lie amidst undifferentiated cells with crystal-violet stained nuclei.
Figure 8B:
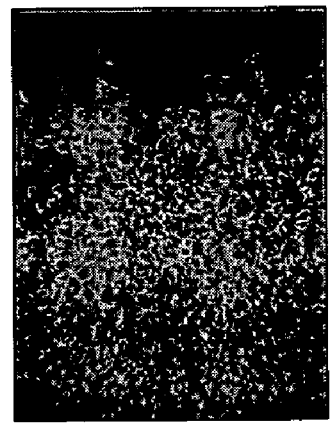
FIGS. 8A-8B show differentiated phenotypes of a Xn-derived hair follicle epithelial cell line.
Figure 8A:
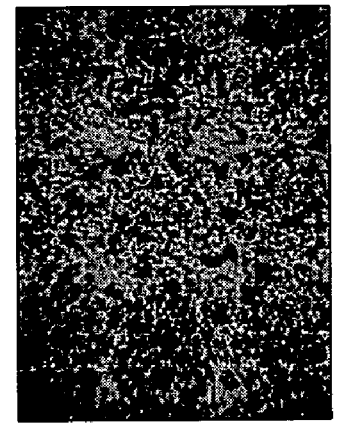
Figure 9A:
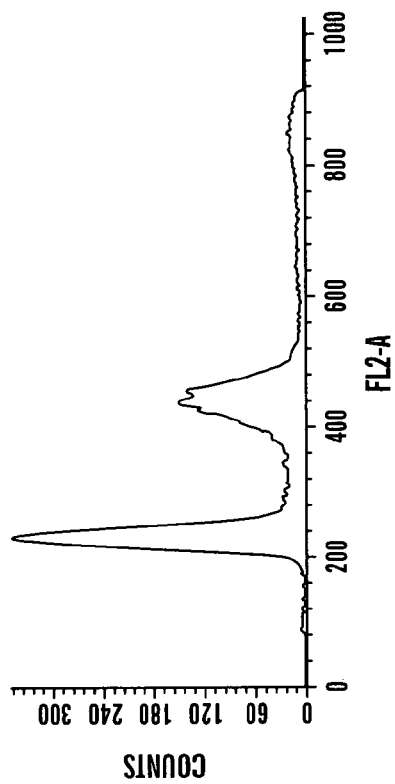
FIGS. 9A-9D show that a colcemid arrest assay (CAA) can detect asymmetric self-renewal in cultures of engineered cell lines. After 24 hours of culture, p53-null cells (FIGS. 9A and 9C) and p53-inducible cells (FIGS. 9B and 9D; i.e., inducible IMPDH down-regulation) grown under conditions that induce asymmetric self-renewal in cultures of p53-inducible cells, were either allowed to continue growth (FIG. 9A and FIG. 9B) or were treated with colcemid (FIG. 9C and FIG. 9D). Shown are flow cytometry histograms from analyses of untreated and treated cultures for propidium iodine fluorescence, indicating relative DNA content.
Figure 9B:
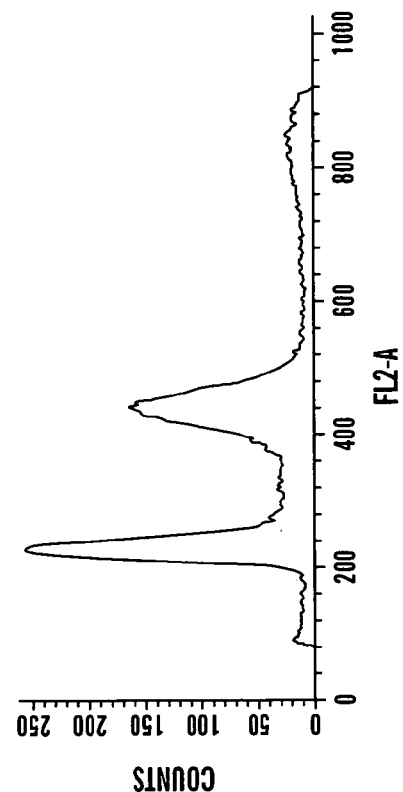
Figure 9C:
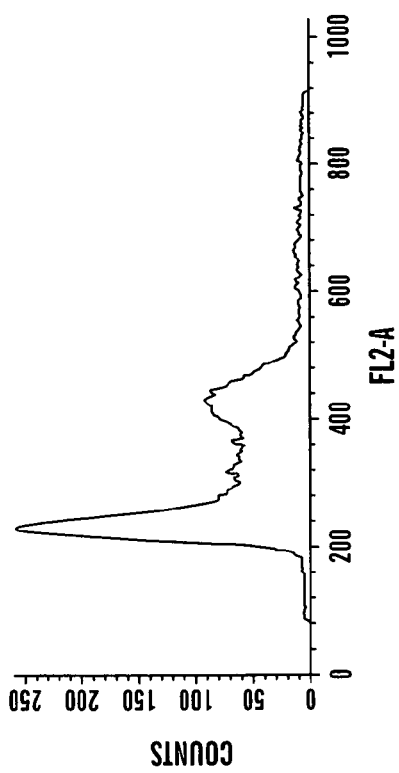
Figure 9D:
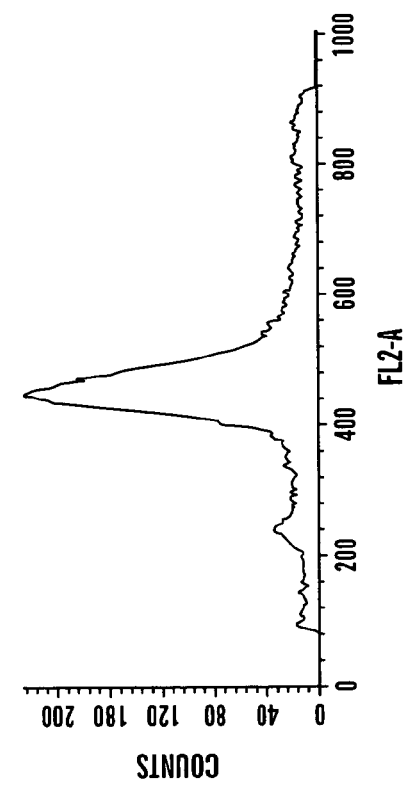
Figure 11A:
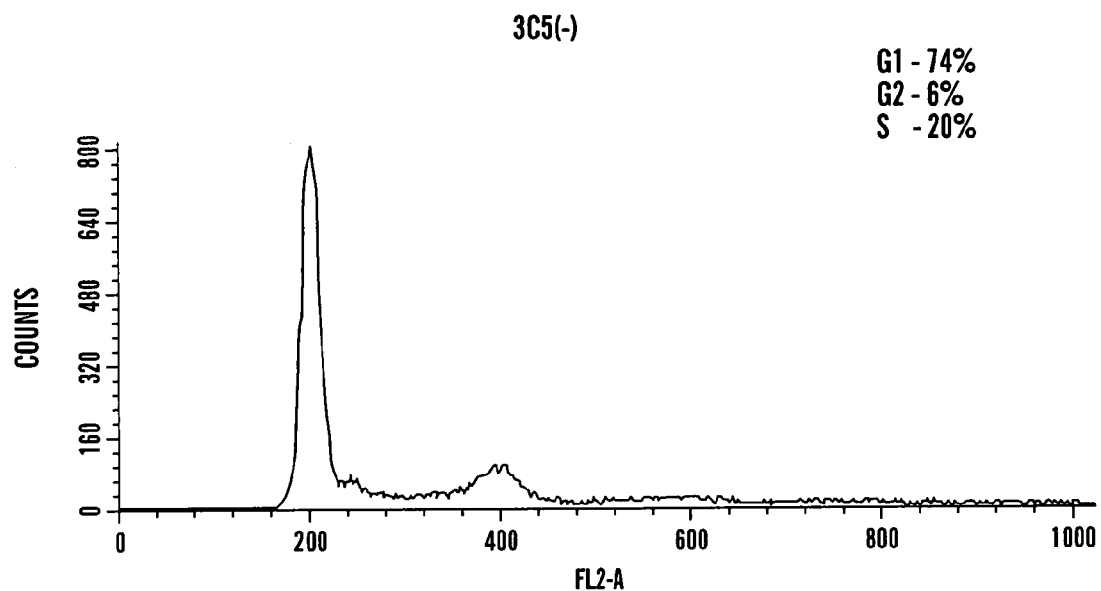
FIGS. 11A-11D show colcemid arrest evidence for asymmetric self-renewal by putative adult mouse hair follicle stem cells. Strain 3C5, a typical xanthine-derived cell strain (FIGS. 11A and 11B) and strain 5B8, a vesicle forming strain (FIGS. 11C and 11D), were cultured in the presence (FIG. 11B and FIG. 11D) and absence (FIG. 11A and FIG. 11C) of the mitotic blocker colcemid for approximately 1 cell generation. Cultures were evaluated by flow cytometry with propidium iodide. The flow cytometry histograms show G1 phase cell peaks (at a relative fluorescent intensity of 200 on the abscissa) that do not progress to a G2/M arrest by colcemid (at 400). These colcemid arrest profiles are indicative of asymmetrically self-renewing adult stem cells that produce non-cycling, differentiating progeny cells continuously. The relative cell cycle fractions are indicated in the top right corner for each histogram.
Figure 11B:
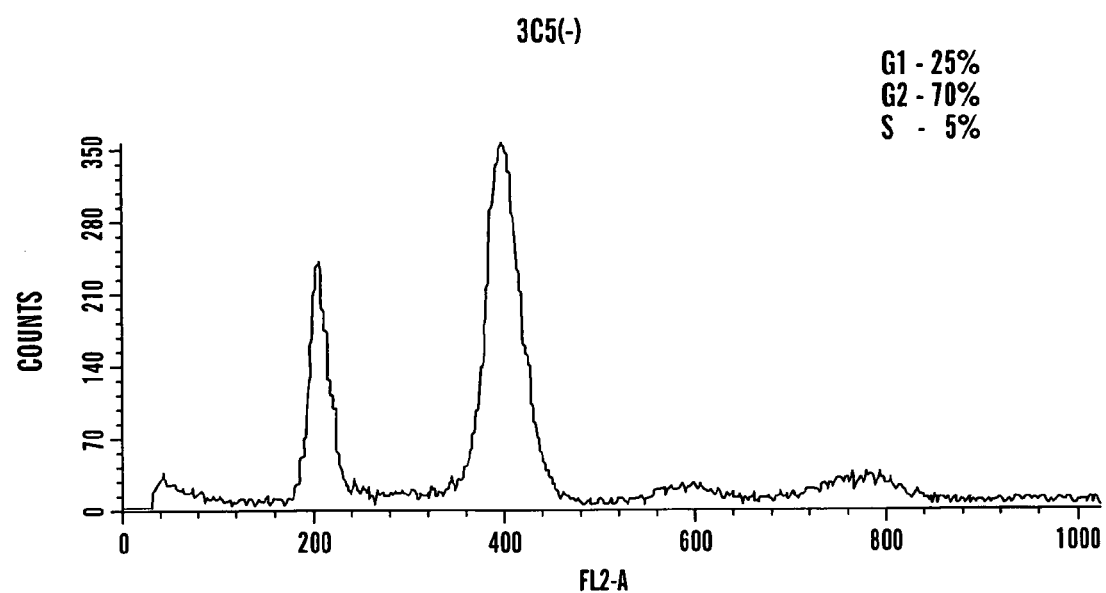
Figure 11C:
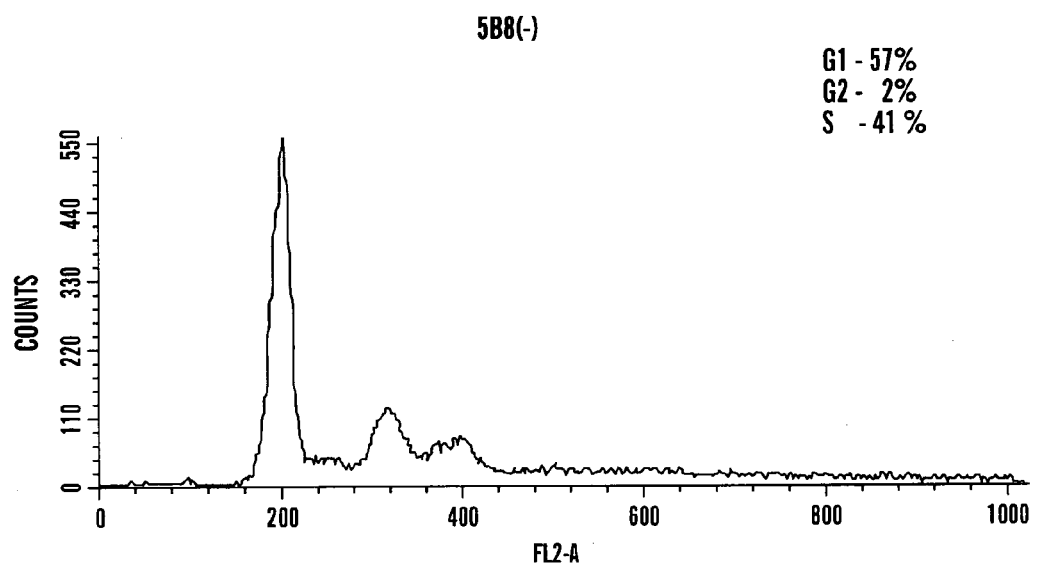
Figure 11D:
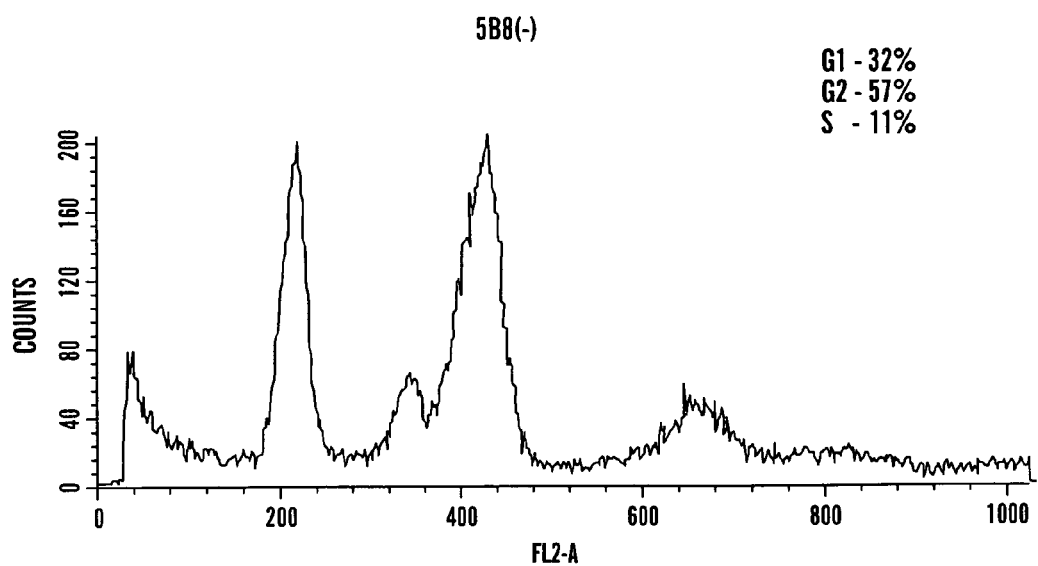

Three different epithelial morphologies are readily seen among the Xn-derived hair follicle epithelial cell lines. The most dramatic of these is exhibited by 3 of the 15 Xn-derived cell lines. As shown in FIG. 8, upon reaching confluency, the lines produce cells with large membrane vesicles. The vesicles are noted to be highly light-reflective and yellowish in color in the light microscope, properties of sebum (Sheu et al., 1999). The appearance of these cells at confluency indicates a need for growth arrest, a common requirement for differentiation. The content of the vesicles can be further evaluated using the lipid dyes like Nile red, Sudan black, and oil red. Such, chemical composition analyses of extracted lipids can confirm the identification of sebum, which is composed of tryiglycerides, wax esters, and squalene (Sheu et al., 1999). These droplets stain positively for oil red.

Example 2

Transgenic Adult Stem Cell Producer Mice

We have generated transgenic mice ubiquitously expressing the xanthine phosphoribosyltransferase (XPRT) gene. We used the gene encoding for XPRT from the protozoan *Leismania donovani*. The XPRT enzyme can convert Xanthine into xanthosine monophosphate, the critical precursor for cellular guanine nucleotides. This enzyme has no mammalian counterpart and its substrate can enter the cell via ubiquitously expressed nucleobase transporters. Therefore, we can control the kinetics of adult stem cells expressing XPRT by supplementing with or depriving the culture medium of xanthine. In the presence of xanthine, XPRT-expressing cells increase their cellular level of guanine nucleotides independently of their normal endogenous pathway involving the conversion of inosine monophosphate to xanthosine monophosphate by the enzyme inosine monophosphate dehydrogenase.

We have generated transgenic mice ubiquitously expressing the XPRT gene under the control of the chicken β-actin/CMV enhancer. We have shown that adult stem cell-enriched populations from skeletal muscle, pancreas or small intestinal epithelium show enhanced proliferation in xanthine-supplemented culture medium when cells are explanted from XPRT-transgenic mice. We have also shown that the culture of pancreatic cells from one of the transgenic lines gives rise to clusters of small cells with large nuclei. This feature is typical of ductal cells, from which a subset is believed to correspond to the pancreatic adult stem cells. The combination of XPRT expression with xanthine-supplementation allows us to efficiently expand adult stem cells from all tissue types, including hair follicles. Access to pure or enriched population of somatic hair follicle stem cells is of great scientific and economic interest for those developing tissue bioengineering protocols and defining hair follicle stem cell properties.

Example 3

Use of a Colcemid Arrest Assay (CAA) to Provide Cell Kinetics Evidence for Derivation of Mouse Hair Follicle Stem Cells The Colcemid Arrest Assay (CAA)

Asymmetric self-renewal is a defining property of adult stem cells. Depending on the extent of division in the non-stem cell lineage, the associated asymmetric cell kinetics can also be used to identify adult stem cells in culture. We have described the use of several assays for the detection of asymmetric cell kinetics in culture, including serial micro-colony analyses (Sherley et al., 1995ab; Lee et al., 2003), time lapse video microscopy (Rambhatla et al., 2001), and fluorescence in situ cytometry (Lee et al., 2003). We have also developed a new method for analysis of asymmetric cell kinetics in cultured cells that is based on flow cytometry detection of the production of non-cycling progeny cells. This development was motivated by our discovery that, even under differentiating conditions, adult hepatic stem cells continue to divide and produce arrested progeny which undergo cell cycle arrest coincident with differentiation (G. G. Crane and J. L. Sherley, in preparation). Therefore, we recognized that an assay that could detect the production of non-cycling cells would also be an assay for adult stem cell asymmetric self-renewal.

The new assay is called the colcemid arrest assay (CAA). We used our engineered cell lines with experimentally controlled asymmetric self-renewal to develop it (Rambhatla et al., 2001; FIG. 9). Cell cultures are treated with the microtubule antagonist colcemid for a complete generation period. Conventional methods for propidium iodine staining and standard flow cytometry are used to quantify the DNA content of cells after colcemid treatment. In the presence of colcemid, cycling cells arrest in mitosis of the cell cycle with 4N DNA content. After one generation period, all previously cycling cells contain this amount of DNA. Therefore, for cell cultures with only symmetrically cycling cells, essentially the entire culture arrests in mitosis with 4N DNA (compare FIGS. 9A and 9C). In contrast, the DNA content of non-cycling cells is unchanged. Since many types of cell cycle arrest occur in G1 phase of the cell cycle, in which the DNA content is 2N, arrested progeny cells are easily distinguished in flow cytometry from previously cycling stem cells that have been arrested by colcemid. Thus, CAA can identify and quantify the cycling stem cell fraction and the arrested differentiated progeny fraction of an asymmetrically self-renewing adult stem cell population (compare FIG. 9B and 9D). Moreover, by performing CAA serially, it is possible to determine the rate of production of arrested progeny. In pilot studies with engineered cell lines, the CAA-determined rates were in good agreement with expectations based on previous lineage-specific cell kinetics assays.

The CAA has good sensitivity, being able to reproducibly detect arrested fractions as low as 10%. However, the specificity of the assay has two limitations. First, if progeny cells arrest in G2 of the cell cycle, which also has a 4N DNA content, they will be obscured by colcemid-arrested cycling cells. This problem is somewhat mitigated by the fact that, in general, G2 cells are a small fraction of cultured cell populations. Thus far, in independent analyses, we have not found G2 to be a significant phase for progeny cell arrest. Second, if arrested cells are produced for reasons besides asymmetric self-renewal (e.g., stochastic differentiation), the CAA cannot make this distinction. Therefore, we use the CAA as a convenient first test for asymmetric self-renewal. If CAA does not indicate production of non-cycling cells, then asymmetric self-renewal is unlikely. When they are detected, then the CAA must be supported with more specific assays like daughter pair analysis (Lee et al., 2003) to establish that adult stem cell lineages are present. Once asymmetric self-renewal is established, it is strong evidence of adult stemness; and thereafter CAA can be used for substantial high volume quantitative cell kinetics evaluations.

Cell Kinetics Evidence for Derivation of Mouse Hair Follicle Stem Cells

As described in Example 1, we expanded stem cells from whisker hair follicles of the adult mouse and prepared stem cell lines. Given the evidence of mixed populations of cycling and differentiating cells in the sebum-producing cell lines, we decided to evaluate them with the CAA. As a positive control, we analyzed our adult rat hepatocyte stem cell line Lig-8, which we have shown by independent lineage analysis to exhibit asymmetric self-renewal. As shown in FIGS. 10A and 10C, Lig-8 cultures show a significant fraction of non-cycling cells in the CAA. Three independently derived sebum-producing hair follicle cell lines show evidence of production of a significant fraction of arrested cells (e.g., see FIGS. 10B and 10D). Combined with the evidence of significant differentiation, these CAA results indicate cultures with a high degree of asymmetric self-renewal, indicative of adult stem cells.

Given the current views of the adult hair follicle stem cells' multi-potency, the sebum-producing cell lines may also produce other types of differentiated hair follicle-derived cell types.

Adult mouse hair follicle stem cell strains 3C5 (a typical xanthine-derived cell strain) and strain 5B8 (a vesicle forming strain) also show in vitro evidence for asymmetric self-renewal in a CAA (See FIGS. 11A-11D). Strain 3C5 (FIGS. 11A and 11B) and strain 5B8 (FIGS. 11C and 11D), were cultured in the presence (FIG. 11B and FIG. 11D) and absence (FIG. 11A and FIG. 11C) of the mitotic blocker colcemid for approximately 1 cell generation. Cultures were evaluated by flow cytometry with propidium iodide. The flow cytometry histograms show G1 phase cell peaks (at a relative fluorescent intensity of 200 on the abscissa) that do not progress to a G2/M arrest by colcemid (at 400). These colcemid arrest profiles are indicative of asymmetrically self-renewing adult stem cells that produce non-cycling, differentiating progeny cells continuously.

REFERENCE

Berardi, A. C., Wang, A., Levine, J. D., Lopez, P., Scadden, D. T. (1995) Functional isolation and characterization of human hematopoetic stem cells. *Science* 267, 104-108.

Bernstein, A., Dick, J. E., Huszar, D., Robson, I., Rossant, J., Magli, C., Estrov, Z., Freeman, M., and Phillips, R. A. (1986) Genetic engineering of mouse and human stem cells. *Cold Spring Harbor Symposia on Quantitative Biology* LI, 1083-1091.

Brenner, M. K. (1996). Gene transfer to hematopoetic cells. *New Engl. J. Med.* 335, 337-339.

Cairns, J. (1975). Mutation selection and the natural history of cancer. *Nature* 255, 197-200.

Cheshier, S. H., Morrison, S. J., Liao, X. and Weissman, I. L. (1999) In vivo proliferation and cell cycle kinetics of long-term self-renewing hematopoetic stem cells. *Proc. Natl. Acad. Sci. USA* 96, 3120-3125.

Collart, F. R., Chubb, C. B., Mirkin, B. L., and Huberman, E. (1992) Increased inosine-5'-phosphate dehydrogenase gene expression in solid tumor tissues and tumor cell lines. *Cancer Res.* 52, 5826-5828.

Dearden, P. and Akam, M. (2000) Segmentation in silico. *Nature* 406, 131 -132.

El-Deiry, W. S., Tokino, T., Velculescu, V. E., Levy, D. B., Parsons, R., Trent, J. M., Lin, D., Mercer, W. E., Kinzler, K. W., and Vogelstein, B. (1993) WAF1, a potential mediator of p53 tumor suppression. *Cell* 75, 817-825.

Epperly, M. W., Bray, J. A., Carlos, T. M., Prochownik, E., and Greenberger, J. S. (1999) Biology of marrow stromal cell lines derived from long-term bone marrow cultures of Trp53-deficient mice. *Radiation Res.* 152, 29-40.

Fuchs, E. and Segre, J. A. (2000) Stem cells: A new lease on life. *Cell* 100, 143-155.

Giaccia, A. J. and Kastan, M. B. (1998) The complexity of p53 modulation: emerging patterns from divergent signals. *Genes & Dev.* 12, 2973-2983.

Goodell, M. A., Brose, K., Paradis, G., Conner, A. S., and Mulligan, R. C. (1996) "Isolation and functional properties of murine hematopoetic stem cells that are replicating in vivo." *J. Exp. Med.* 183, 1797-1806.

Goodell, M. A., Rosenzweig, M., Kim, H., Marks, D. F., DeMaria, M., Paradis, G., Grupp, S. A., Sieff, C. A., Mulligan, R. C. and Johnson, R. P. (1997) Dye efflux studies suggest that hematopoetic stem cells expressin low or undetectable levels of CD34 antigen exist in multiple species. *Nature Med.* 3, 1337-1345.

Gottleib, T. M. and Oren, M. (1996) p53 in growth control and neoplasia. *Biochim. Biophys. Acta* 1287, 77-102.

Greenberger, J. S., Epperly, M. W., Zeevi, A., Brunson, K. W., Goltry, K. L., Pogue-Geile, K. L., Bray, J. and Berry, L. (1996) Stromal cell involvement in leukemogenesis and carcinogenesis. in vivo 10, 1-18.

Gridelli, B. and Remuzzi, G. (2000) Strategies for making more organs available for transplantation. New Engl. J. Med. 343, 404-410.

Grisham, J. W. and Thorgeirsson, S. S. (1997) Liver stem cells. In Stem Cells, C. S. Potten, ed. (San Diego, Calif.: Harcourt Brace & Co.), pp.1-28.

Gu, J. J., Stegmann, S., Gathy, K., Murray, R., Laliberte, J., Ayscue, L., and Mitchell, B. S. (2000) Inhibition of T lymphocyte activation in mice heterozygous for loss of the IMPDH gene. *J. Clin. Invest.* 106, 599-606.

Hauschka, P. V. (1973) "Analysis of nucleotide pools in animal cells" in *Methods in Cell Biology*, Prescott, D. M., ed. Academic Press (New York) Vol. VII, pp. 361-462.

Herrero-Jimenez, P., Thilly, G., Southam, P. J., Tomita-Mitchell, A., Morgenthaler, S., Furth, E. E., and Thilly, W. G. (1998). Mutation, cell kinetics, and subpopulations at risk for colon cancer in the United States. *Mutation Res.* 400, 553-578.

Hollstein, M., Sidransky, D., Vogelstein, B., and Harris, C. C. (1991) p53 mutations in human cancers. *Science* 253, 49-53.

Huang, S., Law, P., Francis, K., Palsson, B. O., and Ho, A. D. (1999) "Symmetry of initial cell divisions among primitive hematopoetic progenitors is independent of ontogenic age and regulatory molecules." *Blood* 94, 2595-2604.

Jackson, R. C., Weber, G., and Morris, H. P. (1975) IMP dehydrogenase, an enzyme linked with proliferation and malignancy. *Nature* 256, 331-333.

Jardim, A., Bergeson, S. E., Shih, S., Carter, N., Lucas, R. W., Merlin, G., Myler, P. J., Stuart, K., and Ullman, B. (1999) Xanthine phosphoribosyltransferase from *Leishmani donovani*. Molecular cloning, biochemical characterization, and genetic analysis. *J. Biol. Chem.* 274, 34403-34410.

Jordan, C. T. and Lemischka, I. R. (1990) Clonal and systemic analysis of long-term hematopoiesis in the mouse. *Genes Dev.* 4, 220-232.

Knudson, A. G. (1992) Stem cell regulation, tissue ontogeny, and oncogenic events. *Seminars in Can. Biol.* 3, 99-106.

Kobayashi, K., Rochat, A., and Barrandon, Y. (1993) Segregation of keratinocyte colony-forming cells in the bulge of the rat vibrissa. *Proc. Natl. Acad. Sci. USA* 90, 7391-7395.

Kornberg, A. (1980) *DNA replication*, ed. 2. W. H. Freeman and Co., San Francisco, Calif.

Latham, K. M., S. W. Eastman, A. Wong, and P. W. Hinds. (1996). Inhibition of p53-mediated growth arrest by overexpression of cyclin-dependent kinases. *Mol. Cell. Biol.* 16, 4445-4455.

Latt, S. A., George, Y. S., and Gray, J. W. (1977) Flow cytometric analysis of bromodeoxyuridine-substituted cells stained with 33258 Hoechst. *J. Histochem. Cytochem.* 25, 927-934.

Lee, H.-S., Crane, G. G., Merok, J. R., Tunstead, J. R., Hatch, N. L., Panchalingam, K., Powers, M. J., Griffith, L. G., and Sherley, J. L. (2003) "Clonal Expansion of Adult Rat Hepatic Stem Cell Lines by Suppression of Asymmetric Cell Kinetics (SACK)", *Biotech. & Bioeng* 83, 760-771.

Lee, H.-S., Sherley, J. L., Chiou, L.-L., Chen, J. J. W., Lai, H.-S., Chiu, C.-C., Chen, C.-H., Huang, G.-T., Sheu, J.-C., and Yang, P.-C. (2004) "Differential Expression of Neogenin and Epithelial Membrane Protein-I in an Adult Rat Liver Stem Cell Line," submitted.

Leong, P.-M., Thilly, W. G., and Morgenthaler, S. (1985) Variance estimation in single-cell mutation assays: comparison to experimental observations in human lymphoblasts at 4 gene loci.

Levine, A. J. and Momand, J. (1990) Tumor suppressor genes: the p53 and retinoblastoma sensitivity genes and gene products. *Biochim. Biophys. Acta* 1032, 119-136.

Lin, D., Fiscella, M., O'Connor, P. M., Jackman, J., Chen, M., Luo, L. L., Sala, A., Travali, S., Appella, E., Mercer, W. E. (1994). Constitutive expression of B-myb can bypass p53-induced Waf1/Cip1-mediated G1 arrest. *Proc. Natl. Acad. Sci. USA* 91, 10079-10083.

Liu, X., Constantinescu, S. N., Sun, Y., Bogan, J. S., Hirsch, D., Weinberg, R. A., and Lodish, H. F. (2000) Generation of mammalian cells stably expressing murine genes at predetermined levels. *Anal. Biochem.* 280, 20-28.

Liu, Y., Bohn, S. A., and Sherley, J. L. (1998a) Inosine-5'-monophosphate dehydrogenase is a rate-determining factor for p53-dependent growth regulation. *Mol. Biol. Cell* 9, 15-28.

Liu, Y., Riley, L. B., Bohn, S. A., Boice, J. A., Stadler, P. B., and Sherley, J. L. (1998b) Comparison of Bax, Waf1, and IMP dehydrogenase regulation in response to wild-type p53 expression under normal growth conditions. *J. Cellular Physiology* 177, 364-376.

Loeffler, M. and Potten, C. S. (1997). Stem cells and cellular pedigrees—a conceptual introduction. In *Stem Cells*, C. S. Potten, ed. (San Diego, Calif.: Harcourt Brace & Co.), pp.1-28.

Matioli, G., Niewisch, H., and Vogel, H. (1970) Stochastic stem cell renewal. Rev. Europ. Etudes Clin. Et Biol. XV, 20-22.

Maurer, S. M., Firestone, R. B., and Scriver, C. R. (2000) Science's neglected legacy. *Nature* 405, 117-120.

Merok, J. L. and Sherley, J. L. (2001) Breaching the Kinetic Barrier to In Vitro Somatic Stem Cell Propagation. J. Biomed. Biotech 1, 24-26.

Mitaka, T., Sato, F., Mizuguchi, T., Yokono, T., Mochizuki, Y. (1999) Reconstruction of hepatic organoid by rat small hepatocytes and hepatic nonparenchymal cells. *Hepatology* 29, 111-125.

Moore, K. A., Ema, H., and Lemischka, I. R. (1997) In vitro maintenance of highly purified, transplantable hematopoietic stem cells. *Blood* 89, 4337-4347.

Murray, A. W. (1971) The biological significance of purine salvage. *Ann. Rev. Biochem.* 40, 811-826.

Nagai, M., Natsumeda, Y., and Weber, G. (1992) Proliferation-linked regulation of type II IMP dehydrogenase gene in human normal lymphocytes and HL-60 leukemic cells. *Cancer Res.* 52, 258-261.

Natsumeda, Y., Ohno, S., Kawasaki, H., Konno, Y., Weber, G., and Suzuki, K. (1990) Two distinct cDNAs for human IMP dehydrogenase. *J Biol. Chem.* 265, 5292-5295. McKay, R. (2000) Stem cells-hype and hope. Nature 406, 361-364.

Neutra, M. and Louvard, D. (1989) "Differentiation of intestinal cells in vitro", In Epithelial *Cells in Culture*, Alan R. Liss, pp. 363-398.

Nias, A. H. W. and Lajtha, L. G. (1965) "Clone size distribution in the study of inhomogeneity of growth rates in tissue culture" in Cell Culture, C. V. Ramakrishnan, ed. (Dr. W. Junk Publishers, Netherlands).

Nishimura, E. K., Jordan, S. A., Oshima, H., Yoshida, H., Osawa, M., Moriyama, M., Jackson, I. J., Barrandon, Y., Miyachi, Y., and Nishikawa, S.-I. (2002) Dominant role of the niche in melanocyte stem-cell fate determination. *Nature* 416, 854-860.

Oshima, H., Rochat, A., Kedzia, C., Kobayashi, K., and Barrandon, Y. (2001) Morphogenesis and renewal of hair follicles from adult multipotent stem cells. *Cell* 104, 233-245.

O'Connor, P. M., Jackman, J., Bae, I., Myers, T. G., Fan, S., Mutoh, M., Scudiero, D. A., Monks, A., Sausville, E. A., Weinstein, J. N., Friend, S., Fornace, Jr., A. J., and Kohn, K. W. (1997) Characterization of the p53 tumor suppressor pathway in cell lines of the National Cancer Institute anticancer drug screen and correlations with the growth-inhibitory potency of 123 anticancer agents. *Cancer Res.* 57, 4285-4300.

Petersen, B. E., Bowen, W. C., Patrene, K. D., Mars, W. M., Sullivan, A. K., Murase, N., Boggs, S. S., Greenberger, J. S., Goff, J. P. (1999) Bone marrow as a potential source of hepatic oval cells. *Science* 284, 1168-1170.

Phillips, R. L., Ernst, R. E., Brunk, B., Ivanova, N., Mahan, M. A., Deanehan, J. K., Moore, K. A., Overton, G. C., and Lemischka, I. R. (2000) The genetic program of hematopoetic stem cells. *Science* 288, 1635-1640.

Poldosky, D. K. (1993). Regulation of intestinal epithelial proliferation: a few answers, many questions. *Am. J. Physiol.* 264, G179-G186.

Potten, C. S. and Grant, H. K. (1998). The relationship between ionizing radiation-induced apoptosis and stem cells in the small and large intestine. *British J. of Cancer* 78, 993-1003.

Potten, C. S. and Morris, R. J. (1988) Epithelial stem cells in vivo. *J. Cell Sci. Suppl.* 10, 45-62.

Powers, M. J., Rodriguez, R. E., Griffith, L. G. (1997) Cell-substratum adhesion strength as a determinant of hepatocyte aggregate morphology. *Biotech. and Bioeng.* 53, 415-426.

Puck, T. T. and Marcus, P. I., J. (1956) Experimental Medicine 103, 653.

Rambhatla, L., Bohn, S. A., Stadler, P. B., Boyd, J. T., Coss, R. A., and Sherley, J. L. (2000). Cellular senescence: ex vivo p53-dependent asymmetric cell kinetics. *J. Biomed. Biotech,* 1, 27-36.

Rambhatla, L., Bohn, S. A., Stadler, P. B., Boyd, J. T., Coss, R. A., and Sherley, J. L. (2001). Cellular senescence: ex vivo p53-dependent asymmetric cell kinetics. *J. Biomed. Biotech* 1, 28-37.

Reisner, Y., Itzicovitch, L., Meshorere, A., and Sharon, N. (1978). Hematopoetic stem cell transplantation using mouse bone marrow and spleen cells fractionated by lectins. *Proc. Natl. Acad. Sci. USA* 75, 2933-2936.

Ross D. T., Scherf, U., Eisen, M. B., Perou, C. M., Rees, C., Spellman, P., Iyer, V., Jeffrey, S. S., Van de Rijn, M., Waltham, M., Pergamenschikov, A., Lee, J. C., Lashkari, D., Shalon, D., Myers, T. G., Weinstein, J. N., Botstein, D., and Brown, P. O. (2000) Systematic variation in gene expression patterns in human cancer cell lines. *Nat. Genet.* 24, 227-235.

Senda, M. and Natsumeda, Y. (1994) Tissue-differential expression of two distinct genes for human IMP dehydrogenase (E.C.1.1.1.205). *Life Sci.* 54, 1917-1926.

Sherley, J. L. (1991) Guanine nucleotide biosynthesis is regulated by the cellular p53 concentration. *J. Biol. Chem.* 266, 24815-24828.

Sherley, J. L. (2002) Asymmetric cell kinetics genes: The key to expansion of adult stem cells in culture. *Stem Cells* 20, 561-572.

Sherley, J. L., Stadler, P. B. and Johnson, D. R. (1995a) "Expression Of The Wildtype p53 Antioncogene Induces Guanine Nucleotide-Dependent Stem Cell Division Kinetics." *Proc. Natl. Acad. Sci. USA* 92, 136-140.

Sherley, J. L., Stadler, P. B. and Stadler, J. S. (1995b) "A Quantitative Method for the Analysis of Mammalian Cell Proliferation in Culture in Terms of Dividing and Non-dividing cells." *Cell Proliferation* 28, 137-144.

Sherley, J. L. (1996) The p53 tumor suppressor gene as regulator of somatic stem cell renewal division. *Cope* 12, 9-10.

Sherley, J. L. (2000). Tumor Suppressor Genes and Cell Kinetics in the Etiology of Malignant Mesothelioma"in Sourcebook of Asbestos Diseases, G. A. Peters & B. J. Peters, eds. Peters and Peters (Santa Monica), Vol. 21, pp. 91-141.

Sherley, J. L., Stadler, P. B., and D. R. Johnson (1995a). Expression of the wildtype p53 antioncogene induces guanine nucleotide-dependent stem cell division kinetics. *Proc. Natl. Acad. Sci.* 92, 136-140.

Sherley, J. L., Stadler, P. B., and Stadler, J. S. (1995b) A quantitative method for the analysis of mammalian cell proliferation in culture in terms of dividing and non-dividing cells. *Cell Prolif.* 28, 137-144.

Sheu, H.-M., Chao, S.-C., Wong, T.-W., Lee, J. Y.-Y., and Tsai, J.-C. (1999) Human skin surface lipid film: an ultrastructural study and interaction with comeocytes and intercellular lipid lamellae of the statum comeum. *Brit. J. Derm.* 140, 385-391.

Smaglik, P. (2000) "Embryo stem-cell work gets NIH go-ahead", *In Nature* 406, p. 925.

Stadler, P. B., Pennacchi, J., and Sherley, J. L. (1994) Inosine-5'-monophosphate dehydrogenase activity is maintained in immortalized murine cells growth-arrested by serum deprivation. *Adv. Enzyme Regul.* 34, 91-106.

Tiedeman, A. A. and Smith, J. M. (1991) Isolation and sequence of a cDNA encoding mouse IMP dehydrogenase. *Gene* 97, 289-293.

Weissman, I. L. (2000) Stem cells: units of development, units of regeneration, and units of evolution. *Cell* 100, 157-168.

Wilson, J. M. (1993). Vehicles for gene therapy. *Nature* 365, 691-692.

All references described herein are incorporated herein by reference.

We claim:

1. A method of proliferating undifferentiated hair follicle cells in vitro, comprising:
   a) isolating undifferentiated hair follicle cells from a mammal; and
   b) culturing said undifferentiated hair follicle cells in a culture medium comprising xanthine under conditions, and for a time sufficient, to result in proliferation of the undifferentiated hair follicle cells.

2. The method of claim 1, wherein said xanthine is present in an amount of 1-5,000 µM.

3. The method of claim 2, wherein said xanthine is present in an amount of 50-1,500 µM.

4. A method for administering undifferentiated hair follicle cells to a subject, wherein said method comprises:
   a) isolating undifferentiated hair follicle cells from said subject or from an individual who is histologically matched to said subject;
   b) culturing said isolated undifferentiated hair follicle cells in a culture medium comprising xanthine for at least 10 days under conditions sufficient to result in proliferation of the undifferentiated hair follicle cells; and
   c) administering said undifferentiated hair follicle cells to said subject.

5. A method for deriving clonal cell lines of undifferentiated hair follicle cells, comprising:
   a) isolating a hair follicle from a mammal;
   b) transecting the isolated hair follicle;
   c) culturing the transected hair follicle in the presence of xanthine to yield a culture of hair follicle epithelial cells;
   d) performing limiting dilution plating on the culture of hair follicle epithelial cells to isolate single undifferentiated hair follicle cells; and
   e) culturing the isolated single undifferentiated hair follicle cells in the presence of xanthine to produce clonally expanded undifferentiated hair follicle cells.

6. The method of any one of claims 1, 4, or 5, wherein the undifferentiated hair follicle cells are somatic hair follicle stem cells.

* * * * *

UNITED STATES PATENT AND TRADEMARK OFFICE
CERTIFICATE OF CORRECTION

PATENT NO. : 7,655,465 B2
APPLICATION NO. : 11/147013
DATED : February 2, 2010
INVENTOR(S) : Sherley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 630 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,655,465 B2
APPLICATION NO. : 11/147013
DATED : February 2, 2010
INVENTOR(S) : James L. Sherley et al.

Page 1 of 1

It is certified that error appears in the above-identified patent and that said Letters Patent is hereby corrected as shown below:

Col. 1, lines 10-15 should read as follows:

"GOVERNMENT FUNDING," please replace the paragraph at column 1, lines 13-15, with the following: "This invention was made with the Government support under Grant No. EEC9843342 awarded by the National Science Foundation. The Government has certain rights in this invention."

Signed and Sealed this
Twenty-sixth Day of July, 2011

David J. Kappos
*Director of the United States Patent and Trademark Office*